(12) United States Patent  
Crosby

(10) Patent No.: US 8,626,260 B2  
(45) Date of Patent: Jan. 7, 2014

(54) EXPANDABLE ELECTRODE PAD

(76) Inventor: William Crosby, Vero Beach, FL (US)

( * ) Notice: Subject to any disclaimer, the term of this patent is extended or adjusted under 35 U.S.C. 154(b) by 80 days.

(21) Appl. No.: 12/870,711

(22) Filed: Aug. 27, 2010

(65) Prior Publication Data

US 2011/0054286 A1    Mar. 3, 2011

Related U.S. Application Data

(60) Provisional application No. 61/237,562, filed on Aug. 27, 2009.

(51) Int. Cl.  
*A61B 5/0408* (2006.01)  
*A61B 5/0416* (2006.01)

(52) U.S. Cl.  
USPC ............ 600/391; 600/392; 600/393; 600/394

(58) Field of Classification Search  
USPC .................................................. 600/391–394  
See application file for complete search history.

(56) References Cited

U.S. PATENT DOCUMENTS

| | | | | |
|---|---|---|---|---|
| 2,943,628 A * | 7/1960 | Howell | ........................ | 600/391 |
| 3,151,619 A | 10/1964 | Sullivan | | |
| 3,409,007 A | 11/1968 | Fuller | | |
| 4,079,731 A * | 3/1978 | Danby | ........................ | 600/392 |
| 4,202,344 A * | 5/1980 | Mills et al. | ..................... | 600/382 |
| 4,233,987 A | 11/1980 | Feingold | | |
| 4,328,814 A * | 5/1982 | Arkans | ........................ | 600/393 |
| 4,353,372 A | 10/1982 | Ayer | | |
| 4,583,549 A * | 4/1986 | Manoli | ........................ | 600/391 |
| 5,327,888 A * | 7/1994 | Imran | ........................ | 600/393 |
| 5,341,806 A * | 8/1994 | Gadsby et al. | ................ | 600/393 |
| 5,813,979 A | 9/1998 | Wolfer | | |
| 6,076,002 A | 6/2000 | Cartmell et al. | | |
| 6,205,346 B1 | 3/2001 | Akiva | | |
| 6,360,119 B1 * | 3/2002 | Roberts | ........................ | 600/509 |
| 6,687,550 B1 | 2/2004 | Doan | | |
| 6,847,836 B1 | 1/2005 | Sujdak | | |
| 7,445,522 B2 * | 11/2008 | Burnes et al. | ................. | 439/725 |
| 7,933,642 B2 * | 4/2011 | Istvan et al. | ................... | 600/509 |
| 2008/0154110 A1 * | 6/2008 | Burnes et al. | ................. | 600/382 |
| 2008/0177168 A1 | 7/2008 | Callahan et al. | | |

* cited by examiner

*Primary Examiner* — Lee S Cohen

(57) ABSTRACT

An expandable electrode pad having a flexible and stretchable base member that may be either expanded or compressed to provide proper positioning for a plurality of electrode distal contacts. Portions of the base member may have perforations that allow one or more sections of the base member to be separated and positioned a greater, non-stretchable distance away from the remaining strip of distal contacts. Additionally, the circuit body may comprise a distal cut zone that provides for freedom of movement of the plurality of distal contacts and a proximal perforated zone that eliminates lead wire entanglements while also allowing for the tearing of perforations between adjacent conductive circuits when a greater reach is required for the proper placement of a distal contact.

17 Claims, 32 Drawing Sheets

LEFT SIDE ADHESIVE BACKING
SCALE: 1" = 2"

RIGHT SIDE ADHESIVE BACKING
SCALE: 1" = 2"

PRESSURE ARM (TOP VIEW)
SCALE: 1" = 2"

PRESSURE ARM (BOTTOM VIEW)
SCALE: 1" = 2"

EXPANDABLE ELECTRODE PAD

CROSS REFERENCE TO RELATED APPLICATIONS

This application claims the benefit of provisional patent application Ser. No. 61/237,562, filed with the USPTO on Aug. 27, 2009, which is herein incorporated by reference in its entirety.

STATEMENT REGARDING FEDERALLY SPONSORED RESEARCH OR DEVELOPMENT

Not applicable.

INCORPORATION-BY-REFERENCE OF MATERIAL SUBMITTED ON A COMPACT DISK

Not applicable.

BACKGROUND OF THE INVENTION

1. Field of the Invention

The present invention relates to a device comprising multiple electrodes and multiple leads, particularly pads and leads for use in taking electrocardiograms wherein a plurality of electrical signals in a patient's body are monitored through his or her skin.

2. Background Art

Electrocardiograph (ECG) monitors and recorders are widely used to obtain biopotential signals containing information indicative of the electrical activity associated with the heart and pulmonary system. To obtain biopotential signals, ECG electrodes are applied to the skin of a patient in various locations and coupled to an ECG monitor. Placement of the electrodes is dependent on the information sought by the clinician.

The placement of the ECG electrodes on the patient has been established by medical protocols. The most common protocols require the placement of the electrodes in a 3-lead, a 5-lead or a 12-lead configuration. A 3-lead configuration requires the placement of three electrodes; one electrode adjacent each clavicle bone on the upper chest and a third electrode adjacent the patient's lower left abdomen. A 5-lead configuration requires the placement of the three electrodes in the 3-lead configuration with the addition of a fourth electrode adjacent the sternum and a fifth electrode on the patient's lower right abdomen. A 12-lead configuration requires the placement of 10 electrodes on the patient's body. Four electrodes, which represent the patient's limbs, include the left arm electrode (LA), the right arm electrode (RA), the left leg electrode (LL), and the right leg electrode (RL). Six chest electrodes (V1-V6 leads) are placed on the patient's chest at various locations near the heart. Three additional references are constructed from measurements between the right arm and left arm (Lead I), the right arm and the left leg (Lead II) and the left arm to left leg (Lead III). The ten electrodes provide 12 measurement points consisting of I, II, III, AVR, AVL, AVF, and V1-V6 with the right leg electrode typically used as a ground.

The electrodes, after being positioned on the patient, connect to an ECG monitor by an ECG lead set. The distal end of the ECG lead set, or portion closest to the patient, connects to each electrode (alternatively, the electrodes may be integrated into the distal end of the ECG lead set) and receives biopotential signals from the body. The proximal end of the ECG lead set connects to the ECG input connector and supplies the biopotential signals received from the body to the ECG monitor.

Proper placement of the ECG electrodes and proper connections of the ECG electrodes to the ECG lead sets is critical for obtaining the correct biopotential signals. Clinicians often have difficulty connecting ECG lead sets to ECG electrodes because the individual wires of the ECG lead set often become entangled or because the clinician must determine which individual wire connects to each electrode. In addition, the individual wires of the ECG lead sets are often long and cumbersome resulting in patient discomfort.

Issues with placement of electrodes and connection of the ECG lead set are often compounded during emergency situations. First responders and clinicians often place ECG electrodes on accident victim or heart attack sufferers to establish the medical condition. Any delay may result in adverse consequences. Other emergency treatments may require the rapid removal of ECG electrodes further compounding the issues with entanglement and re-connection.

The present application provides an expandable multiple electrode device having multiple leads and methods of use thereof for preventing the aforementioned problems. Prior art attempts have consistently failed to provide a beneficial and efficient solution to such problems. Such prior art devices include U.S. Pat. No. 3,151,619 to Sullivan that focuses on providing an electrode with a self-contained quantity of electrolyte paste confined within a surrounding band or strip of pressure-sensitive adhesive seal that is adaptable to irregular surfaces.

U.S. Pat. No. 4,233,987 to Feingold comprises electrodes for use in taking electrocardiograms by a multiple electrode pad formed as an elongate, narrow, curved strip with the electrodes arranged in a curvilinear relation to one another. The pad readily assumes the shape of the thorax or chest of a man, woman, or child at several desirable application sites, such as precordially, for routine or emergency use. The strip may be perforated or otherwise weakened in lines between the electrodes for tearing of the strip to separate the electrodes for individualized placement.

U.S. Pat. No. 6,205,346 to Akiva comprises an electrode apron for ECG which is comprised of an apron cast from flexible material to be placed over the chest of the patient, ten electrodes inlaid within the apron in predetermined places wherein six of the said electrodes are located at predetermined distances between the ribs, two under each shoulder and two at both sides of the stomach. Either curved or spiraled conductors are cast within flexible material and each conductor is connected to an electrode. A multiple-pronged cable feeds each of the conductors and includes a connector for connecting the apron to any standard ECG measuring device. The apron also has straps and a belt for tightening the apron on the body of the patient, locating the electrodes of the apron in their required locations for ECG tests.

U.S. Pat. No. 6,847,836 to Sujdak comprises an ECG electrode chest pad particularly adapted for use in emergency room situations having upper fit portions with upper limb electrodes, and elongated central or medial base fit portion with a plurality of precordal unipolar electrodes and lower fit portions with lower limb electrodes, said electrodes being attached to leads which are internal to the base chest pad and terminate into at least one lead branch adapted to plug into an ECG monitor and having a perforation in the base pad material such that one group of electrodes may be separated from a second group of electrodes to facilitate ease of patient monitoring and complimentary medical procedures.

U.S. Pat. Pub. No. 2008/0177168 to Callahan et al. comprises an ECG lead set including an ECG electrode assembly and a lead set hub. The ECG electrode includes at least one electrode configured to receive biopotential signals from a patient, a plug connector for connecting said ECG electrode assembly, a web, connected between the at least one electrode and the plug connector and configured to form an electrical connection therebetween. The lead set hub includes at least one receptacle configured to receive the plug connector of the ECG electrode assembly.

Electrodes of the prior art are typically provided in the form of standard fixed strips. However, a standard fixed strip of electrodes does not fit all patients due to variations in patient size, gender, weight, and other physical factors. The devices of the prior art do not allow for movement of the electrodes to allow for proper placement on different people having varying chest sizes; do not allow for exact placement of all the electrodes; and do not allow for electrodes to be separated or placed as a one-piece unit. The devices of the prior art also do not allow for a female person to remain wearing her undergarments while applying the electrode pad; and furthermore the devices of the prior art do not allow for "V4R" (V4R is a position on the body that is mid-clavicular over the fifth intercostal space and the R represents the patient's right side) to be obtained with the same electrode. These prior art fixed strips of electrodes must be sized to the patient and do not allow for movement to lengthen the distance between electrodes as is provided for by the present invention.

Herein is described a device that allows for the electrodes to be stretched farther apart or pressed closer together as needed allowing the device to fit virtually all patients except for potentially the very small. This electrode pad comprises electrodes on a flexible and stretchy material allowing for speedy and accurate placement. This electrode strip can be stretched apart or pressed closer together for an accurate fit for children and adult patients of a wide range of sizes. The present invention provides a multitude of benefits including but not limited to faster performance of 12 lead electrocardiograph, facilitating application and decreasing application time, increasing wire management by reducing/eliminating tangles, improving readings due to less artifacts, increasing adhesion due to larger application area, improving female patient modesty by application around worn garments, facilitating evaluation of V4A (right side heart attack), providing a relatively low cost of manufacture for addition of significant functional benefits, providing a one-size-fits-all stretchable device allowing for both speed and accuracy in use, and the like.

BRIEF SUMMARY OF THE INVENTION

The present invention comprises a device and method of use that has one or more of the following features and/or steps, which alone or in any combination may comprise patentable subject matter.

In accordance with one embodiment of the present invention, an expandable electrode pad comprising a base member, wherein the base member is composed of a stretchable material, and a plurality of distal contacts. Additional embodiment of the expandable electrode pad may further comprise a conductive circuit comprising a distal end electrically connected to the plurality of distal contacts and a proximal end comprising a plurality of proximal contacts; wherein the conductive circuit is printed onto circuit enclosure material and the plurality of distal contacts are connected to the conductive circuit such that the base member is capable of being stretched to increase the distance between each of the plurality of distal contacts and the conductive circuit is separable at perforations located between at least a portion of the length of each conductive circuit that electronically communicates with each of the plurality of distal contacts, wherein the conductive circuit transfers electrical signals to an output device at the plurality of proximal contacts.

DETAILED DESCRIPTION OF THE INVENTION

Herein is described an invention that allows for electrodes, for instance electrocardiogram electrodes but generally any medical electrode type or use including but not limited to electrocardiogram, electroencephalogram, pain relief, and muscle stimulation, to be stretched farther apart or pressed closer together as needed allowing the device to fit virtually all patients except potentially the very small. Electrodes may perform the function of detecting and transmitting electric pulses from the body surface of a patient to a unit that processes the electrical pulses; electrodes may also perform the function of transmitting electrical pulses to the body, as is done, for instance, in electrotherapy applications. The electrode pad of the present invention comprises electrodes on a base member composed of flexible and stretchy material that provides for speedy and accurate electrode placement by allowing the electrodes to be "stretched" to a desired location on the body, even reaching underneath clothing if desired, and therefore overcoming the above described deficiencies of the prior art. The present electrode strip can be stretched apart or pressed closer together for an accurate fit for children and adult patients of a wide range of sizes and can therefore be utilized to accommodate variations in patient size, gender, weight, and other physical factors.

Figure 16:
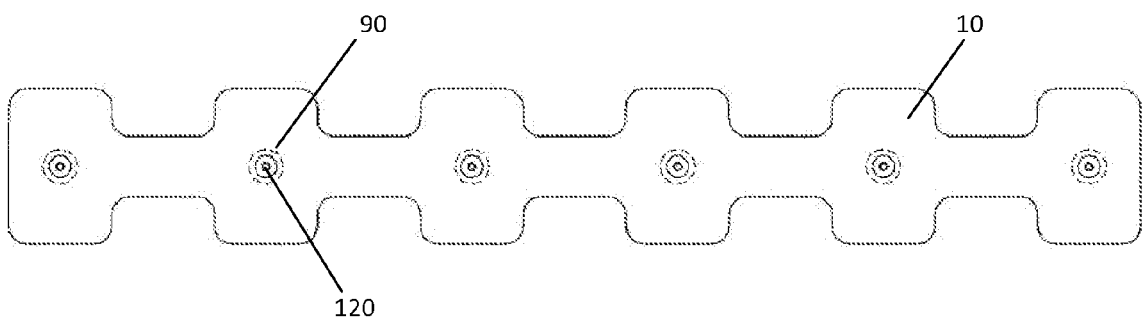
FIG. 16 depicts a bottom planar view of the "ambulance" embodiment of the present invention.
Figure 17:
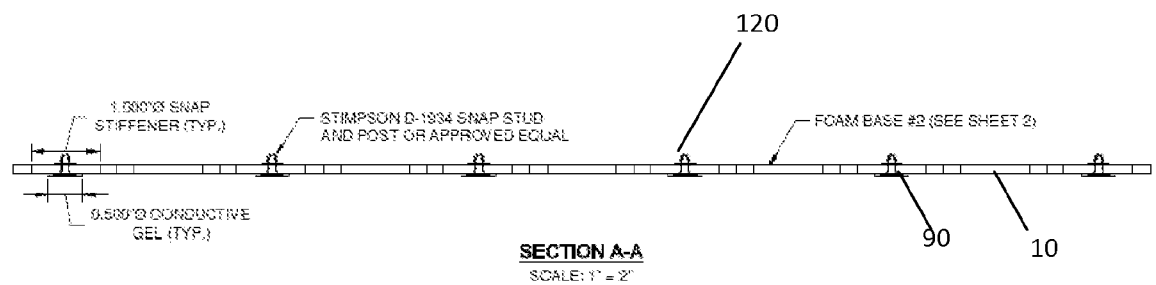
FIG. 17 depicts a side view of the "ambulance" embodiment of the present invention.

This device may generally comprise three primary components the circuit body 20 (see FIGS. 1-2), the base member 10 (see FIGS. 3-4), and a plurality of electrodes (see FIGS. 5-11). FIGS. 12-15 depict potential embodiments of a base member 10 associated with a plurality of electrodes and FIGS. 16-17 depict one embodiment of a device of the present invention comprising a base member 10, a circuit body 20, and a plurality of electrodes.

Figure 1:
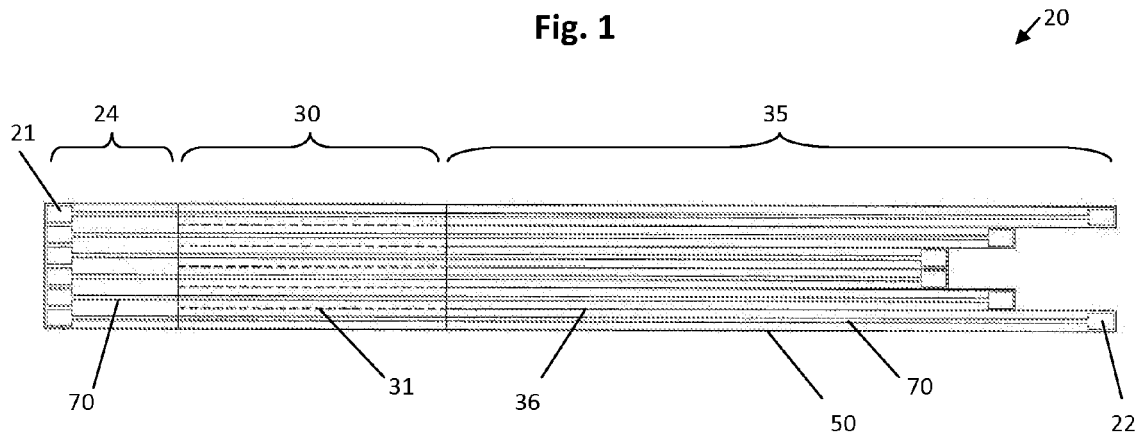
FIG. 1 depicts a bottom planar view of an exemplary embodiment of a circuit body of the present invention.
Figure 2:
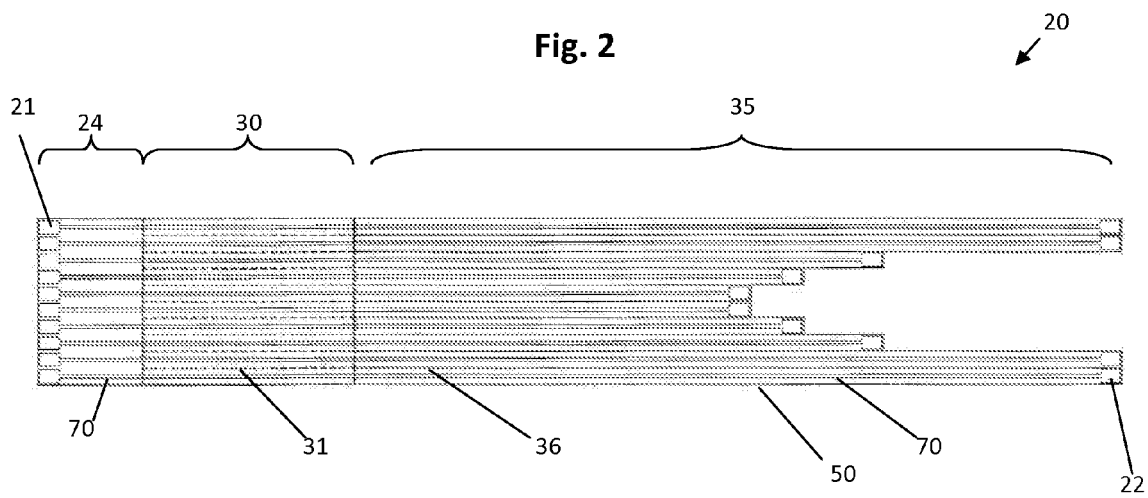
FIG. 2 depicts a bottom planar view of another exemplary embodiment of the circuit body of the present invention.

The circuit body 20, as shown in FIGS. 1-2, is preferably printed by any methods known in the art and capable of producing flexible circuits and may be configured as a wire bundle, a plurality of discrete wires, or a wireless architecture wherein the flexible circuits attached to a wireless sending or receiving unit thus eliminating the need for a patient to be directly wired to electrical signal monitoring equipment. For the printed circuit embodiment, the conductive circuit 70 may be printed or attached on a non-conductive medium or circuit enclosure material 50 such as plastic, silicon, rubber, cloth, paper or other material available to be printed stamped or fitted with a circuit 70 as is known in the art. Any portion of the printed conductive circuit 70 can be centered upon the circuit material 50, so that no portion of the printed conductive circuit 70 touches any other portion of the printed conductive circuit 70 in such a way as to create a short-circuit. The printed conductive circuit 70 may additionally be protected with a protecting agent such as paint, wax, plastic, silicon, elastomer, or any other non-conductive material known within the art.

The circuit body's 20 non-stretched size may be any size appropriate for the application. However, in a preferred embodiment the non-stretched circuit body 20 may be in the range of approximately one (1) inch to twenty (20) inches in width, but more preferably in the range of approximately one (1) inch to four (4) inches in width. In a preferred embodiment, the non-stretched length of the circuit body 20 may be in the range of approximately six (6) inches to twenty-four (24) inches, but more preferably comprises a length of approximately fourteen (14) inches. In a preferred embodiment, the height of the circuit body 20 may be in the range of approximately one five-hundredth (1/500) of an inch to one half (1/2) inch, but more preferably comprises a height of approximately one three-hundredth (1/300) of an inch. While dimensions are described herein, it is understood that the present invention is not dependent upon, and therefore not limited by, any particular set of dimensions and embodiments of the invention may be of any size appropriate for the application.

As shown in FIGS. 1-2, the circuit body 20 may comprise any number of separate signal pathways of conductive circuits 70. In a preferred embodiment, the number of separate conductive circuits 70 is in the range between two (2) and twenty (20) separate conductive circuits 70, wherein the most preferred number of separate conductive circuits 70 is six (6). The proximal end of the circuit body 20 may further comprise a plurality of proximal contacts 21 that may be capable of or configurable to communicate with any cardiac or electrical monitoring device known within the art. The distal end of the circuit body 20 may comprise a plurality of distal contacts 22, wherein each distal contact 22 may either itself act as an electrode or be connectable to an electrode for detecting and/or transmitting electric pulses from the body surface of a patient.

The length of the circuit body 20 may comprise a variety of structural zones. The most proximal end of the circuit body 20 may comprise an optional fused zone 24 starting from and including the plurality of proximal contacts 21 and extending along the length of the circuit body 20 for a predetermined length. Within the fused zone 24, the plurality of separate conductive circuits 70 may be disposed in a flat planar configuration within each of the conductive circuits 70 is fused to the one or two immediately adjacent conductive circuit(s) 70. A perforated zone 30 may then be located immediately distal to the fused zone 24 or the perforated zone 30 may start from and include the plurality of proximal contacts 21 if a fused zone 24 is omitted from the circuit body 20 configuration. Perforations 31 or scores allow the individual conductive circuits 70 to be easily torn apart or separated from the circuit body 20 thereby allowing the device 200 to be stretched by its length and/or width. A cut zone 35 of the circuit body 20 may then be disposed immediately distal to the perforated zone 30. The cut zone 35 comprises separate conductive circuits 70 that have no physical connections to any other conductive circuit 70 and/or the circuit enclosure material 50 of any other conductive circuit 70 within the cut zone 35 of the circuit body 20. Thus, the cut zone 35 provides "loose" and unrestricted individual conductive circuits 70 that may be freely manipulated to a most beneficial position wherein the perforated zone 30 comprises the more proximal portion of these conductive circuits 70 wherein the conductive circuits 70 are releasably bundled together by perforations 31 located within the circuit enclosure material 50 between each adjacent conductive circuit 70. When the freedom of movement provided by the cut zone 35 is insufficient, perforations 31 of at least a portion of the perforated zone 30 of one or more conductive circuits 70 may be torn to provide additional freedom of movement to the distal end of a conductive circuit 70. The novel fused zone 24/perforated zone 30/cut zone 35 (see FIGS. 1-2 and 31-32) and the perforated zone 30/cut zone 35 configurations of the circuit body 20 provide a solution for lead wire entanglement issues thereby speeding up the proper placement of electrodes for emergency responders and all other medical practitioners.

In a preferred embodiment having a circuit body 20 with a perforated zone 30/cut zone 35 configuration, the lengths of the respective perforated zone 30 and cut zone 35 are approximately thereby providing a circuit body 20 with a proximal half having a plurality of adjacent conductive circuits 70 releasably joined by perforations 31 and a distal half having the plurality of conductive circuits 70 cut away from each other and freely moveable relative to each other. As an example, a twelve (12) inch long circuit body 20 may comprise a proximal six (6) inch fused zone 24 and a distal six (6) inch cut away zone 35. The scope of the present invention in not limited to zones of only equivalent lengths since the present invention contemplates and includes all zones lengths being capable of independent selection.

As shown in FIG. 16, the distal end of the circuit body 20 is attached to the base member 10 material and/or the electrodes at the plurality of distal contacts 22 and the proximal end of the circuit body 20 comprises a plurality of proximal contacts 21 that may be adapted or configured to be compatible with specific connectors and/or preferred cardiac and/or electrical monitoring devices.

Within the circuit body 20 each conductive circuit 70 may comprise a separate and smaller pathway. In a preferred embodiment, each separate pathway or conductive circuit 70 may be in the range of approximately one sixty-fourth (1/64) of an inch to approximately one half (1/2) inch in width, but in a more preferred embodiment each separate pathway or conductive circuit 70 may be approximately fifty one thousandths (51/1000) of an inch in width and comprise a length equivalent to the length of the circuit body 20. In alternate embodiments of the present invention the circuit body 20 may comprise an optional component. Without the circuit body 20 the base member 10 may be equipped with an electrode such as a snap 120, another printed single circuit, or both to allow for use of the electrode without the described circuit body 20.

The base member 10 preferably comprises a foam adhesive or foam tape, but can be constructed of any flexible and stretchy material such as silicon, plastic, rubber, elastic, or other stretchable material known within the art. Many such materials are well known in the art of electrodes and are described in U.S. patent application Ser. No. 11/152,321, which is incorporated herein by reference in its entirety. The base member 10 has an adhesive on the bottom side of the base member 10 that allows the base member 10 to be attached to human skin. The base member 10 is sized to allow enough contact with skin to maintain adhesion and to allow stretching for larger individuals. In a preferred embodiment, the non-stretched length of the base member 10 may be in the range of approximately six (6) inches to twenty-six (26) inches, but more preferably is approximately seventeen (17) inches. In another preferred embodiment, the non-stretched width of the base member 10 may be in the range of approximately one (1) inch to four (4) inches, but more preferably is approximately two inches. In still another preferred embodiment, the non-stretched height of the base member 10 may be in the range of approximately one five-hundredth (1/500) of an inch to one half (1/2) inch, but more preferably is approximately one thirty-second (1/32) of an inch.

Figure 3:
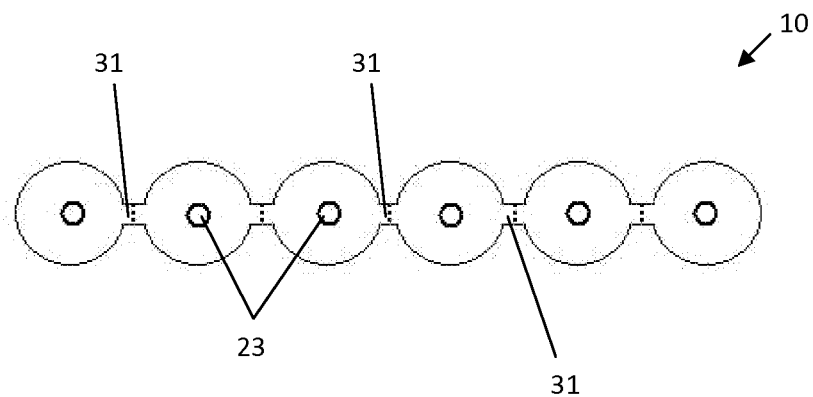
FIG. 3 depicts a top planar view of an exemplary embodiment of a base member of the present invention.
Figure 4:
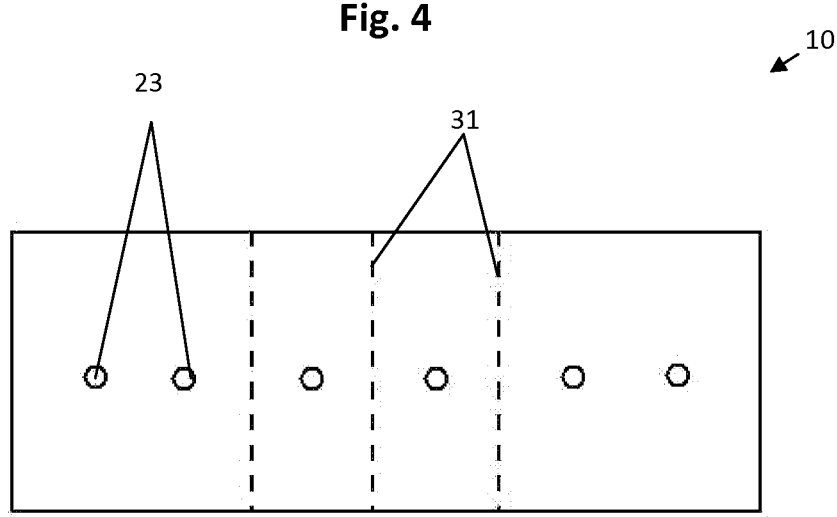
FIG. 4 depicts a top planar view of another embodiment of the base member of the present invention.
Figure 14:
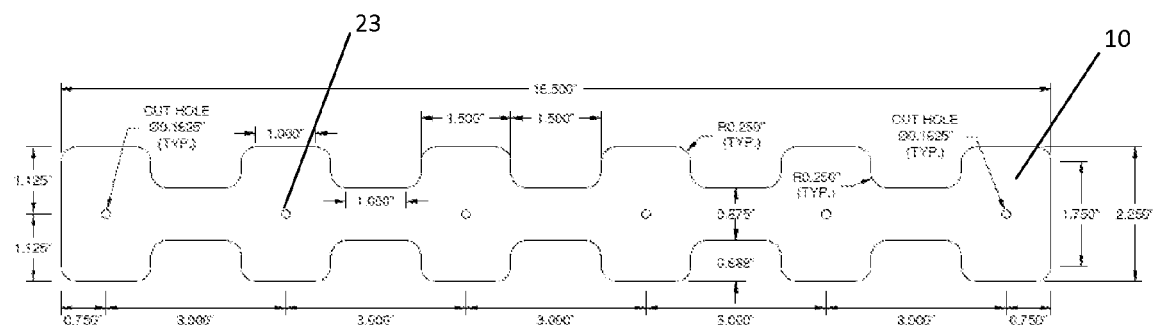
FIG. 14 depicts a top planar view of a base member embodiment of an "ambulance" embodiment of the present invention.
Figure 15:
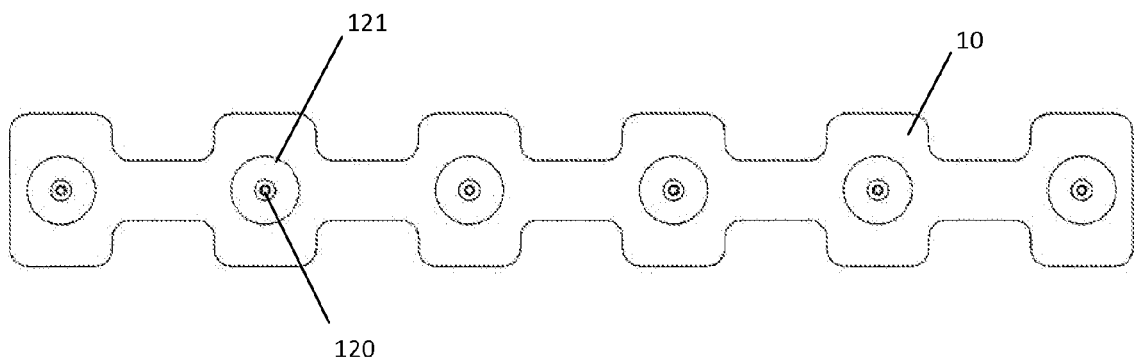
FIG. 15 depicts a top planar view of the "ambulance" embodiment of the present invention.

The shape of the non-stretched base member 10 is preferably configured as shown in FIGS. 14-15, but the base member 10 may comprise any relaxed shape and can thereafter take on any shape due to its stretchable characteristics. The non-stretched base member 10 may also comprise other shapes such as scalloped or oval configurations (see FIG. 3). Regardless of the shape or configuration of the non-stretched base member 10, the benefits of incorporating a perforated zone 35 having perforation 31 may be extended to base members 10 of all such shapes and configurations as shown by FIGS. 3-4. The base member 10 may be shaped to allow for stretching and placement of the base member 10 and electrode at various angles without wrinkles forming in the base member 10 material. As shown in FIG. 4, an exemplary base member 10 may comprise three sets of perforations 31, between the V2 and V3 contact, between the V3 and V4 contact and again between the V4 and V5 contact. These perforations 31 allow for the easy tearing of the base member 10 material to allow for separate adhesion times or for ease of adhesion and/or placement. Such a configuration of perforations 31 also allow for lead V4 to be placed on the right side of the patient's body. The base member 10 can contain other perforations 31 to allow further separation of the electrodes. The base member 10 may contain a plurality of contact apertures 23 for allowing the plurality of distal contacts 22 of the circuit body 20 to pass through the base member 10 material. In a preferred embodiment, the base member 10 may incorporate two (2) to thirteen (13) distal contacts 22.

Figure 5:
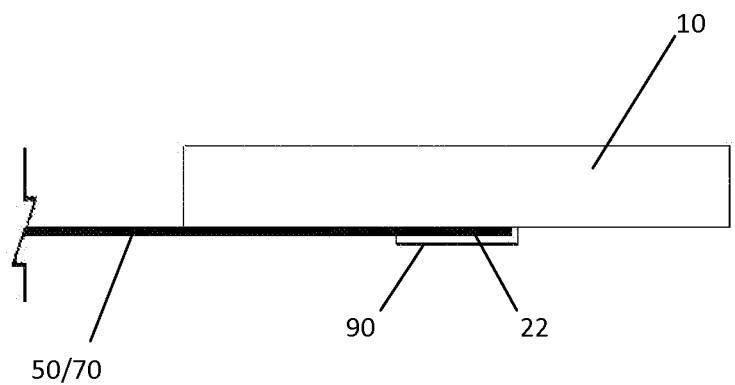
FIG. 5 depicts a schematic side view of an exemplary embodiment of an electrode of the present invention.

As shown in FIGS. 5-11, the plurality of electrodes that attach to the surface of a patient's skin may comprise at least several embodiments. FIG. 5 depicts a generalized embodiment where the conductive circuit 70 and the circuit enclosure material 50 are disposed parallel to and adjacent the bottom surface of the base member 10. In such a configuration, each of the plurality of distal contacts 22 of the circuit body 20 may act as the electrode for receiving and/or transmitting electrical signals to or from the patient's skin. A conductive medium 90 may cover the distal contact 22 and may enhance the reception and/or transmission of the electrical signal. To assist in keeping the base member 10, and thereby the electrode, in its proper position an adhesive layer may also be applied to the bottom surface of the base member 10 and adhere to a patient's skin. Releasable adhesive backing 41 (such as those found on a BANDAID™ bandage) may protect the adhesive layer when the electrode is not in use but such releasable adhesive backing 41 may then be peeled away when the electrode is ready to be deployed.

Figure 6:
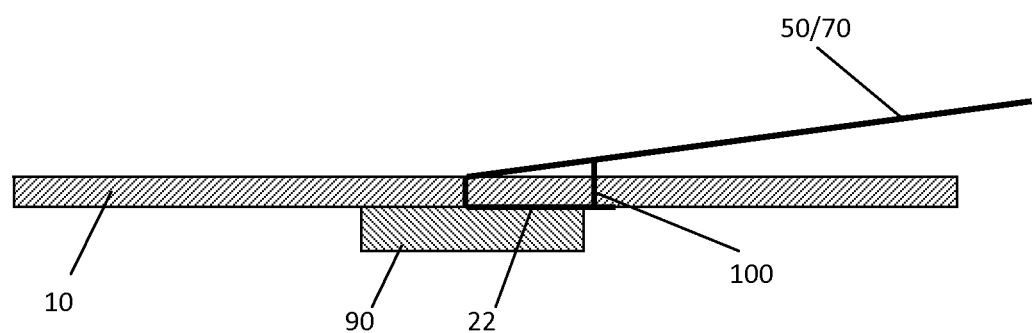
FIG. 6 depicts a schematic side view of another embodiment of the electrode of the present invention.
Figure 7:
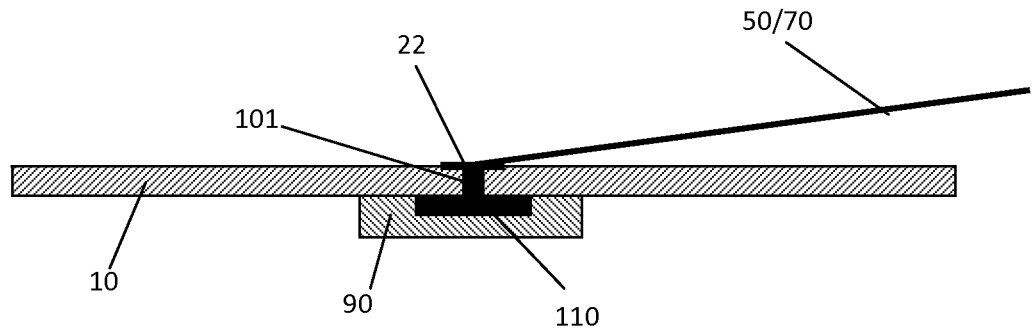
FIG. 7 depicts a schematic side view of still another embodiment of the electrode of the present invention.
Figure 8:
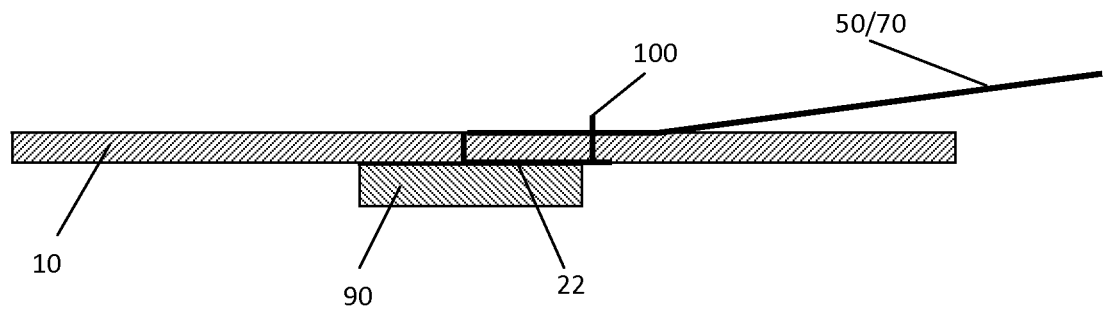
FIG. 8 depicts a schematic side view of still another embodiment of the electrode of the present invention.

FIGS. 6 and 8 depict electrode embodiments wherein the distal contacts 22 of the circuit body 20 may extend through the base member 10 and contact the skin under the base member 10 thereby forming the electrode. A conductive medium 90 may be disposed on a portion of the lower surface of the base member 10 and covering the distal contact to assist in electrical signal transfer. The conductive medium 90, as shown in FIGS. 5-11, can be liquid, dry, gel or powder but is preferably a gel-based material. In a preferred embodiment, the conductive medium 90 may be primarily a flat, circular configuration having a thickness in the range of approximately one thirty-second (1/32) of an inch to one quarter (1/4) of an inch, wherein the most preferred embodiment has a thickness of approximately one sixteenth (1/16) of an inch. In a preferred embodiment, the diameter of the conductive medium 90 is approximately one half (1/2) of an inch but may be in the range between approximately one quarter (1/4) of an inch to three quarters (3/4) of an inch in diameter. The conductive medium 90 may also comprise rectangular, triangular, or oval configurations having similar surface areas coverage when applied.

In a preferred embodiment, the base member 10 preferably contains space for six (6) distal contacts 22 (see FIGS. 14-17), but may contain as many as twenty (20) distal contacts 22. These distal contacts 22 are preferably spaced equally across the base member 10 in a line but can be staggered or unequally spaced. The designation of each distal contact 22 may be labeled on the base member 10 or on the circuit enclosure material 50 surrounding each respective conductive circuit 70. The distal contacts 22 may be connected using any connective methods including but not limited to adhesives, soldering, sewing, pinching, clamping, melting, and any other connection methods known within the art.

Figure 9:
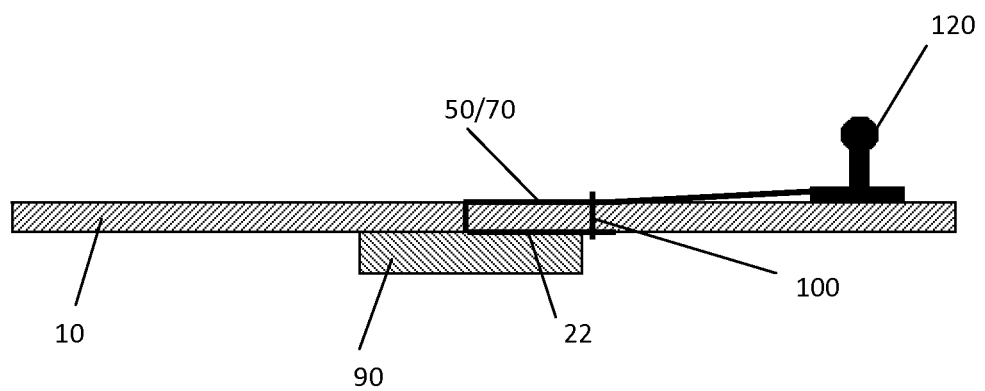
FIG. 9 depicts a schematic side view of still another embodiment of the electrode of the present invention.

Preferably the electrodes may be formed by having the distal contact 22 of each conductive circuit 70 extend through the base member 10 and fold back under itself to expose the distal contact 22 surface so that the conductive medium 90 may be deposited onto the underside of both the base member 10 and the distal contact 22 at the same location or time (see FIGS. 6, 8, and 9). A non-conductive retention body 100 may be used to attach the distal contact 22 back to the conductive circuit 70 or the circuit enclosure material 50 to maintain the distal contact 22 in position and prevent it from being retracted back though the base member 10.

In another embodiment, as shown in FIG. 7, the conductive circuit 70 may also be attached to a conductive disc 110 that extends through the base member 10 via a conductive connector 101. Conductive medium 90 may be applied to the underside of both the conductive disc 110 and the base member 10.

Figure 10:
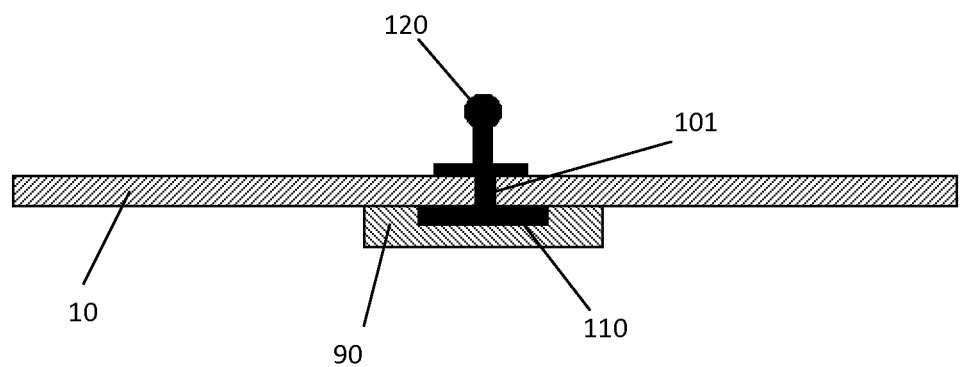
FIG. 10 depicts a schematic side view of still another embodiment of the electrode of the present invention.
Figure 11:
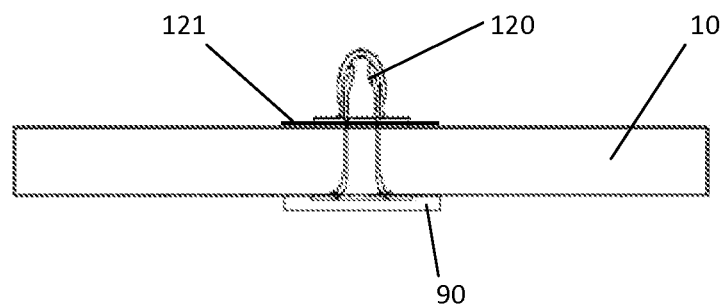
FIG. 11 depicts a schematic side view of yet still another embodiment of the electrode of the present invention.
Figure 12:
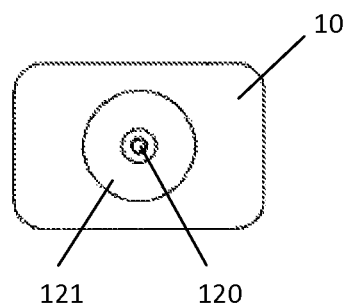
FIG. 12 depicts a top planar view of an electrode configuration of the present invention.
Figure 13:
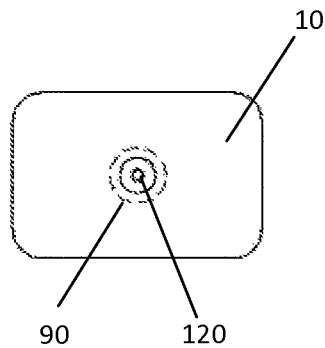
FIG. 13 depicts a bottom planar view of the electrode configuration of the present invention from FIG. 12.

The base member 10 and the distal contacts 22 of the present invention may be used with a vast majority of the lead electrocardiogram units available today. As shown in FIGS. 10-11, such use may necessitate one minor modification wherein a snap 120 structure is used in place of the distal contact 22 where the conductive circuit 70 may connect to the electrode. The electrode embodiment of FIG. 10 comprises a snap 120 extending through the base member 10 via a conductive connector 101 to a conductive disc 110 disposed on the bottom surface of the base member 10 wherein a conductive medium 90 may overlay the conductive disc 110 and a portion of the bottom surface of the base member 10. A distal contact 22 of the circuit body 20 may then be complimentarily configured to removably mate with the snap 120 when electric signals are to be received by and/or transmitted from the electrode. The electrode embodiment of FIG. 11 is highly similar to the embodiment depicted in FIG. 10 but further comprises a snap stiffener 121 being disposed along the upper surface of the base member 10 to facilitate use of the snap 120 connection. An alternate electrode embodiment is shown in FIG. 9, wherein a snap 120 is used in combination with a length of conductive circuit 70. In such an embodiment, the snap 120 may remain on the upper surface of the base member 10 and a conductive circuit 70 may extend from the snap 120 through the base member 10 in a similar fashion to the embodiments depicted in FIGS. 6 and 8. In this manner, the advantages of using a removable snap 120 connection between the circuit body 20 and an electrode of a circuit body 20 may be maintain even if the snap 120 cannot be located (for whatever reason) at the optimal or desired distal contact 22 location. FIGS. 12-13 depict an embodiment of an individual electrode comprising a snap 120 and a snap stiffener 121 associated with the base member 10.

Figure 18:
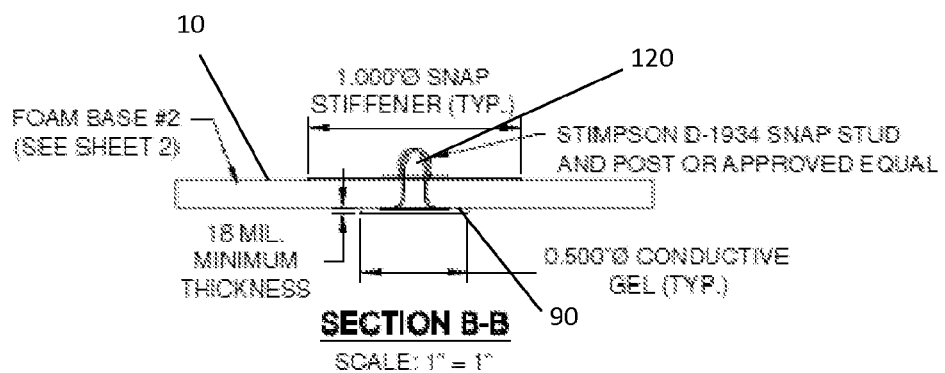
FIG. 18 depicts an end view of the "ambulance" embodiment of the present invention.
Figure 19:
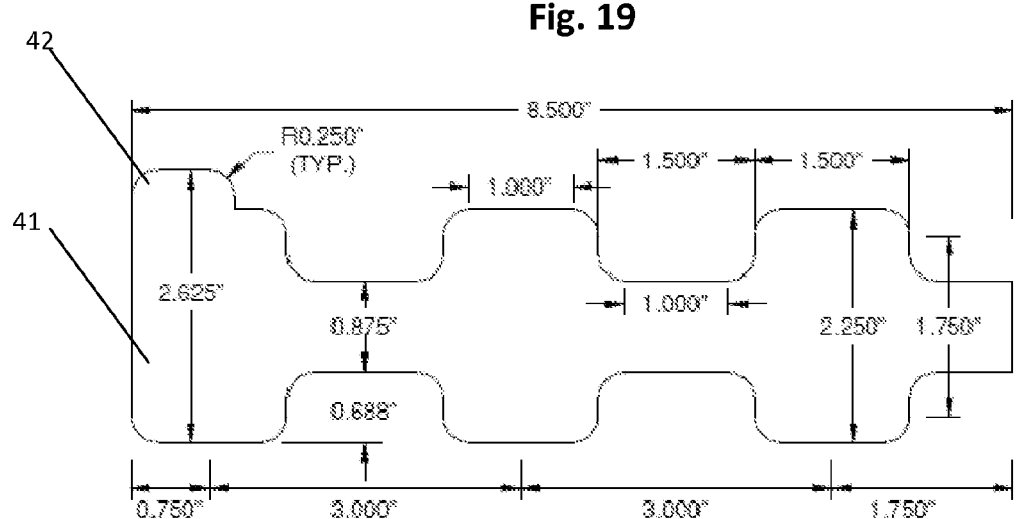
FIG. 19 depicts a top view of one embodiment of releasable adhesive backing of the present invention.
Figure 20:
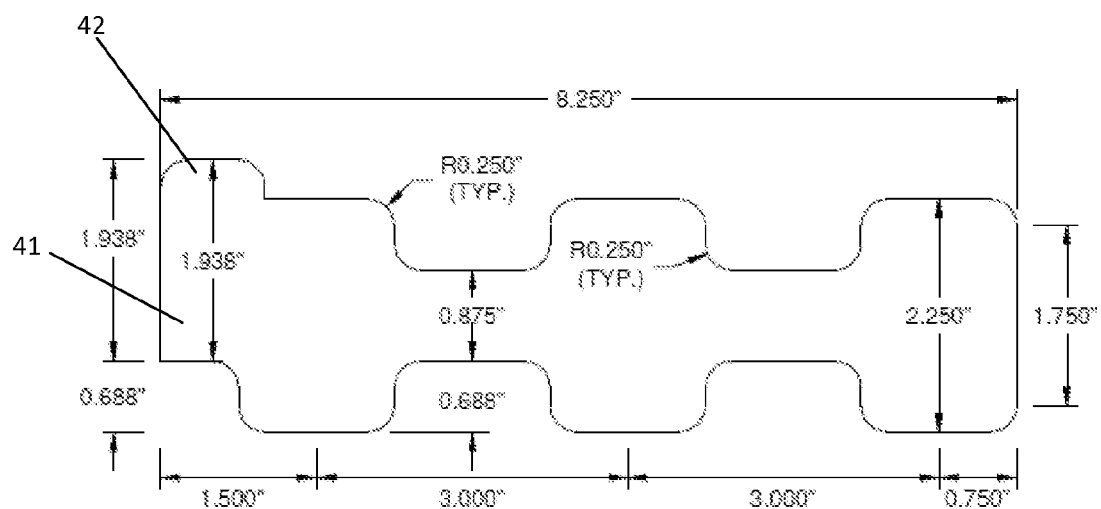
FIG. 20 depicts a top view of another embodiment of releasable adhesive backing of the present invention.
Figure 21:
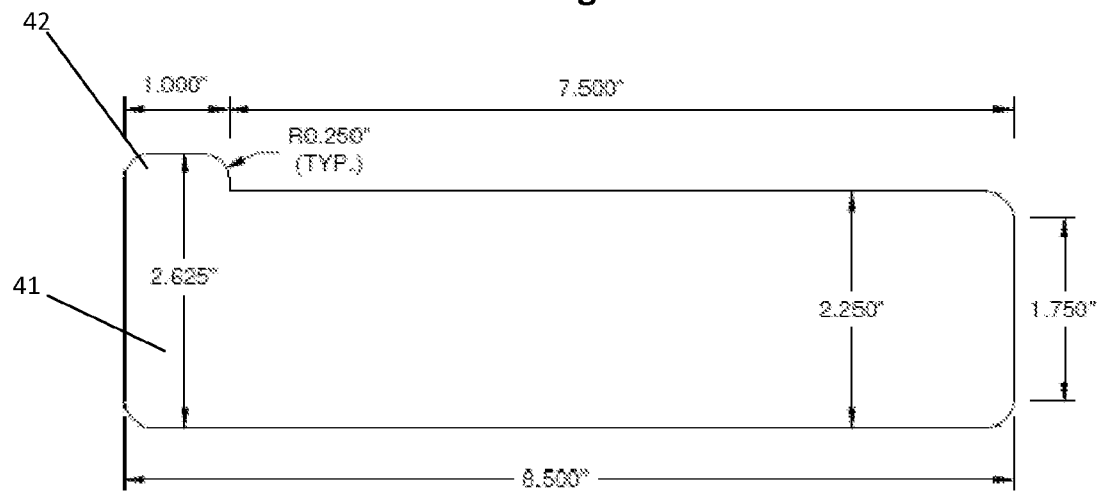
FIG. 21 depicts a top view of another embodiment of releasable adhesive backing of the present invention.
Figure 22:
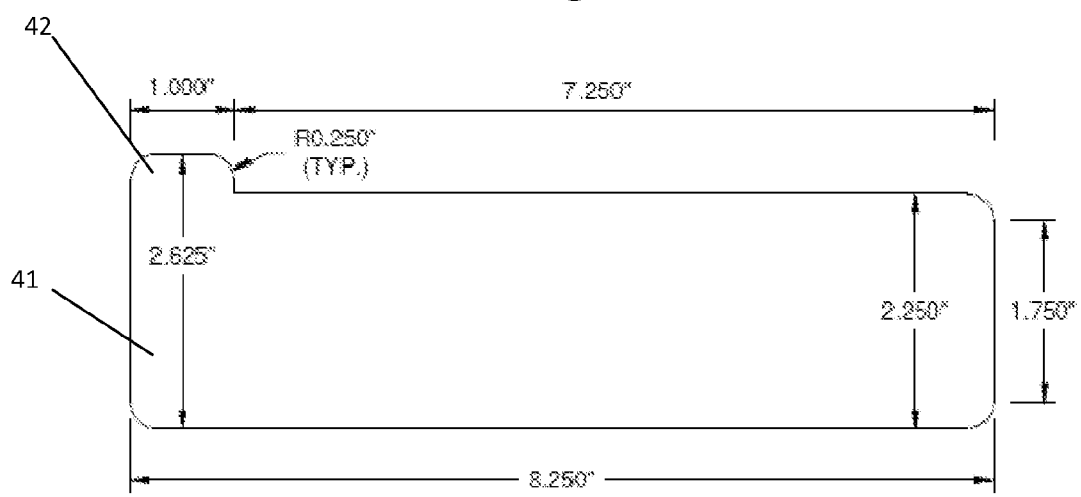
FIG. 22 depicts a top view of still another embodiment of releasable adhesive backing of the present invention.
Figure 23:
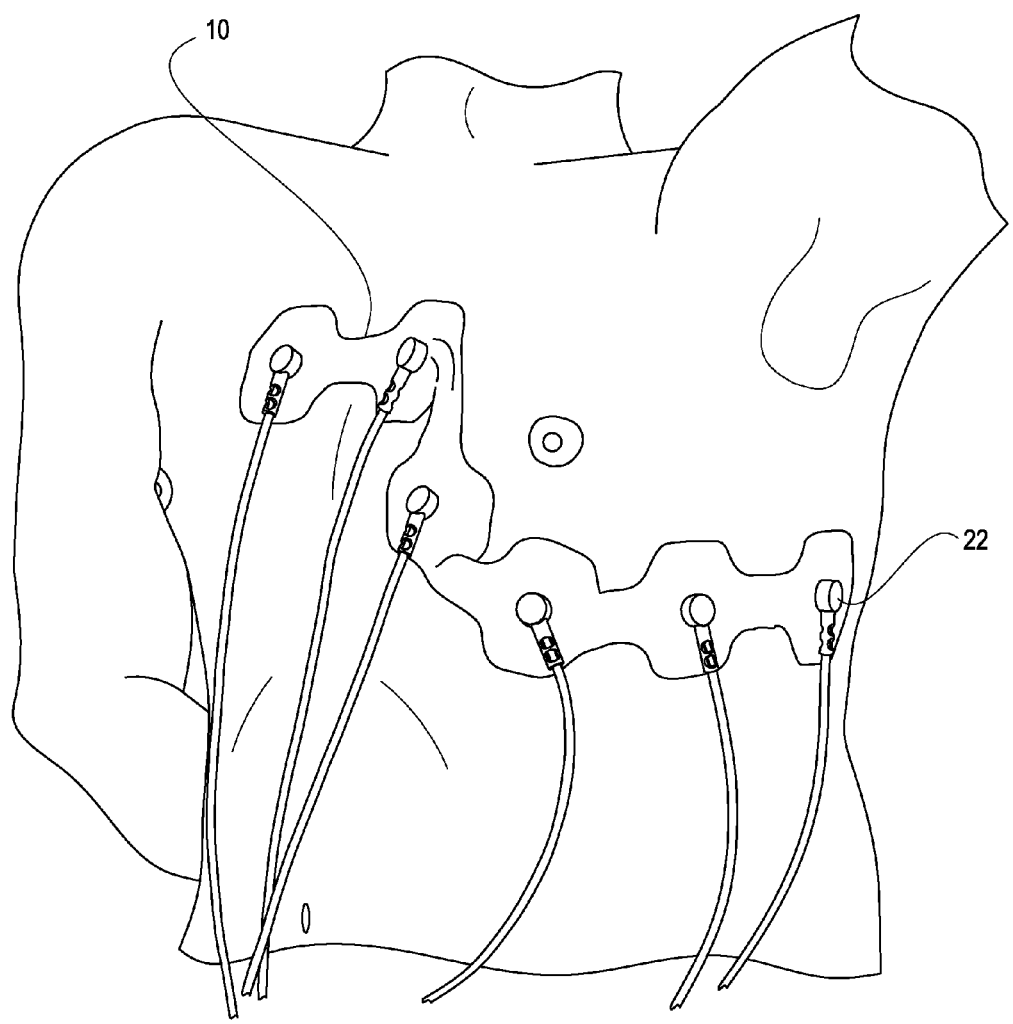
FIG. 23 depicts a perspective view of the "ambulance" embodiment of the present invention adhered to a patient.

FIGS. 14-18 depict an ambulance embodiment of a similar base member 10 structure having six (6) electrodes within the flexible base member 10 wherein the same snap 120 and snap stiffener 121 configurations are replicated across the six (6) electrodes. FIG. 14 depicts an embodiment of the base member 10 having six (6) contact apertures 23 through which an electrode such as a snap 120 or distal contact 22 of the circuit body 20 may pass through. FIG. 15 illustrates a top view of such an embodiment wherein the electrode comprises a snap 120 and a snap stiffener 121 disposed between at least a portion of the snap 120 and the base member 10 to assisting in both connecting and disconnecting the snap 120 from the conductive circuit 70. In alternate embodiments, the snap stiffener 121 may be of a unitary construction with the snap 120 in the form of an extended flange about the snap 120 or the like. FIG. 16 depicts a bottom view of the ambulance embodiment wherein a bottom surface of the snap 120 extends through the base member 10 and may receive and/or transmit an electrical signal from or to the patient's body. A conductive medium 90 may be disposed over the bottom surface of the snap 120 to assist or enhance the electrical signal. FIGS. 17 and 18 show a side view and an end view, respectively, of the ambulance embodiment. As seen in FIG. 17, a portion of the base member 10 located between each respective electrode or snap 120 may be stretched to increase the distance between the respective electrodes or snaps 120 as the plurality of electrodes are placed on the skin of the patient. All base members 10 of the present invention may comprise stretchable material allowing for at least linear expansion of the base member 10, lines of perforations 31 incorporated through the base member 10 between adjacent electrodes or snaps 120, or a combination thereof allowing for both stretching of the material of the base member 10 and physical separation of portions of the base member 10 at the perforations 31 if necessary. FIG. 23 illustrates an ambulance embodiment of the present invention applied to the skin of a patient. The flexible, stretchable base member 10 has been stretched and contorted to properly locate or fit the snaps 120 onto the patient's body. Releasable adhesive backing(s) 41 have been removed from the bottom surface of the base member 10 to expose an adhesive for securing the bottom surface of the base member 10 to the skin. The snap 120 disposed though the base member 10 has been coupled to the complimentary distal contact 22 of the circuit body 20 to allow for communication of electrical signals to and/or from the skin.

Figure 24:
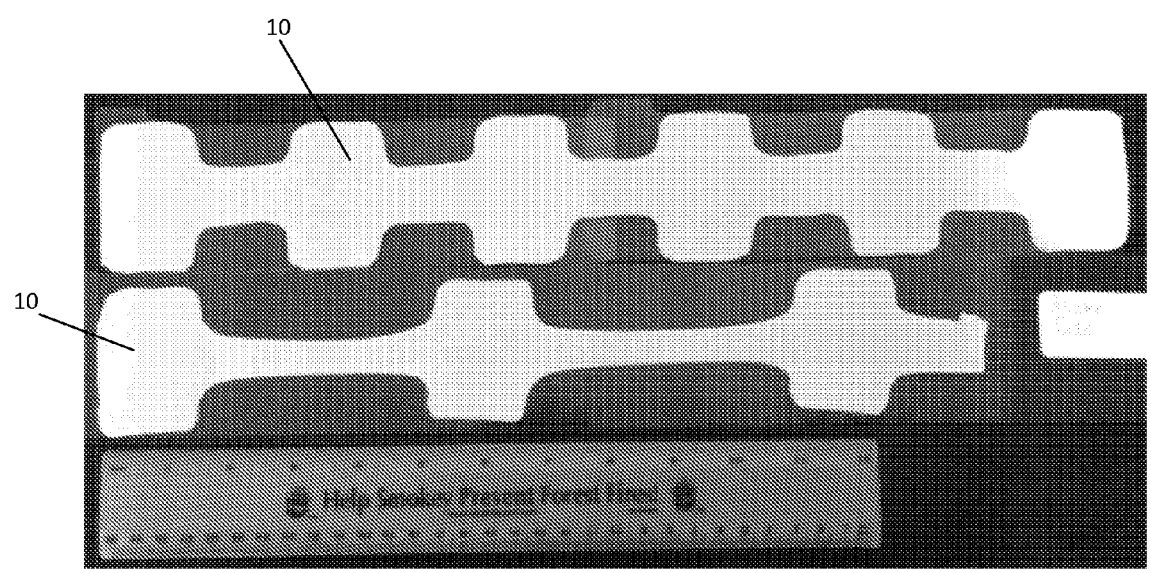
FIG. 24 depicts a top planar view of showing the variation between one embodiment of a base member of the present invention both before stretching and after stretching.

FIG. 24 illustrates the stretching characteristics of the base member 10 of the present invention. The top-most example is a non-altered embodiment of a base member 10 capable of seating six (6) electrodes. The bottom-most example depicts the same type base member 10 after a tensile force has caused the adjacent electrode locations to be stretched a greater distance apart from one another as may be necessary for proper location of multiple electrodes on patients having abnormal or larger than average bodily dimensions. As an alternative to or in combination with the stretchable characteristics of the base member 10, base members 10 of the present invention may further comprise perforations 31 between the respective electrode areas or nodes along the base member 10 (see FIGS. 50-51). In this manner, the respective electrodes disposed along the base member 10 may be physically stretched apart from each other due to the stretchable physical characteristics of their material and/or torn apart at the perforations 31 to allow for a greater reach of an electrode as needed.

FIGS. 19-22 illustrate a couple embodiments of releasable adhesive backings 41 that may be placed on the bottom surface of the base member 10 to protect the adhesive and/or conductive medium 90 deposited on the bottom surface of the base member 10. The releasable adhesive backings 41 may take any number of configurations including a single releasable adhesive backing 41 that may cover the entirety of the bottom surface of the base member 10 to a plurality of releasable adhesive backings 41 that may each cover a respective repeating electrode region or "node" of any configuration having a repeating pattern. The scope of the present invention further includes all intermediary lengths of releasable adhesive backing 41 that may cover one, two, three (see FIGS. 19-22), four, five, six, or any increasing number of electrode areas or nodes. The adhesive backing 41 may end in the middle or partially into an electrode area or node and need not be limited to full electrode area or node coverage. To assist in removing the releasable adhesive backing(s) 41, a tab 42 of the adhesive backing 41 may extend beyond the boundary of the base member 10 shape to allow a user to grasp it in a quick and rapid manner. Additionally, at least a portion of an adhesive backing 41 may overlap at least a portion of an adjacent adhesive backing 41 thereby allowing the overlapped portion to be more easily grasped by a user. The illustrated adhesive backings 41 cover three electrode areas or nodes and follow the shape of the base member 10 with the exception of a tab 42 portion. A user may remove only a portion of an adhesive backing 41 or fewer than all multiple adhesive backings 41 to allow for placement of one or more electrodes while the remainder of the electrodes retain their backing 41 and will not adhere to the patient's skin while other electrodes are being placed. The scope of the present invention comprises all configurations of releasable adhesive backing 41 and such backings 41 are not limited or restricted to only those that mimic the shape of the associated base member 10.

Figure 25:
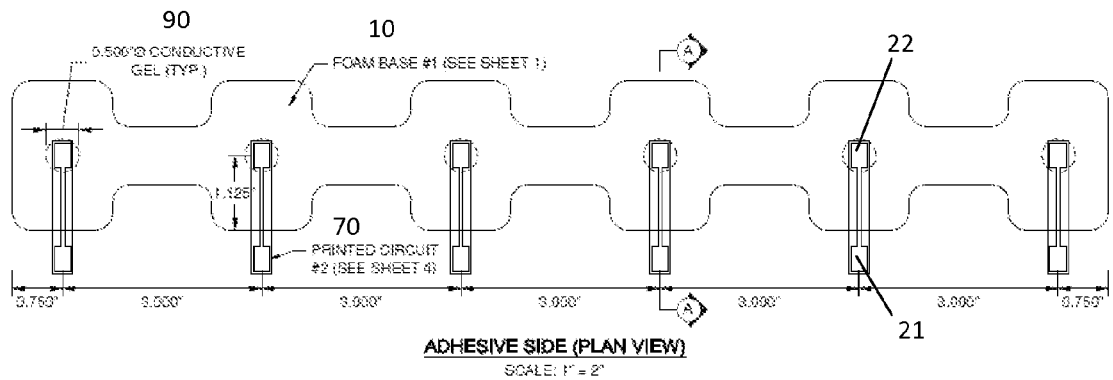
FIG. 25 depicts a bottom planar view of an "office" embodiment of the present invention.
Figure 26:
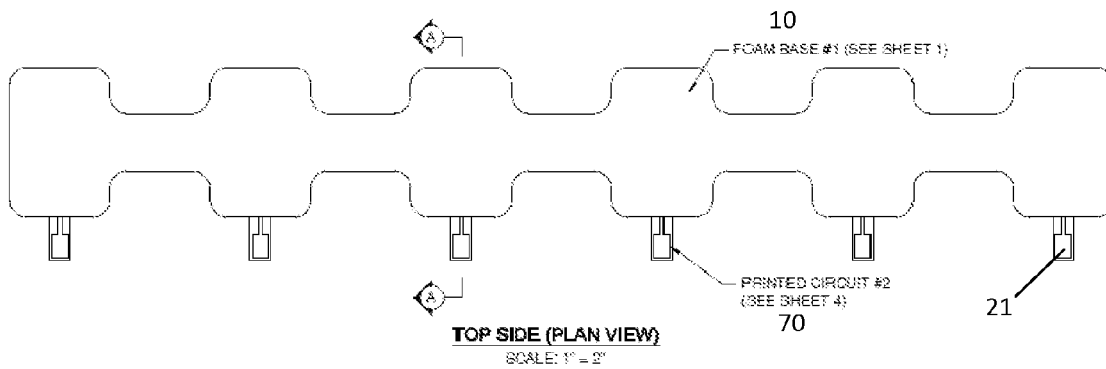
FIG. 26 depicts a top planar view of the "office" embodiment of the present invention.
Figure 27:
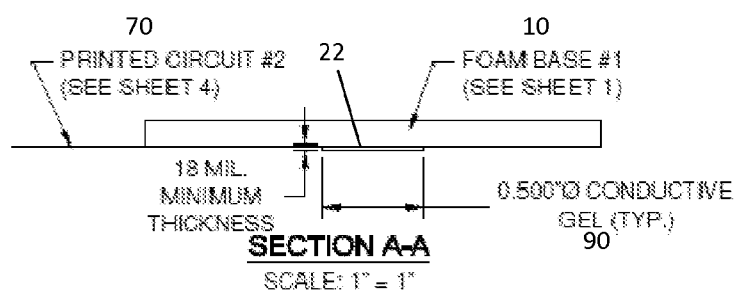
FIG. 27 depicts a side view of the "office" embodiment of the present invention.
Figure 50:
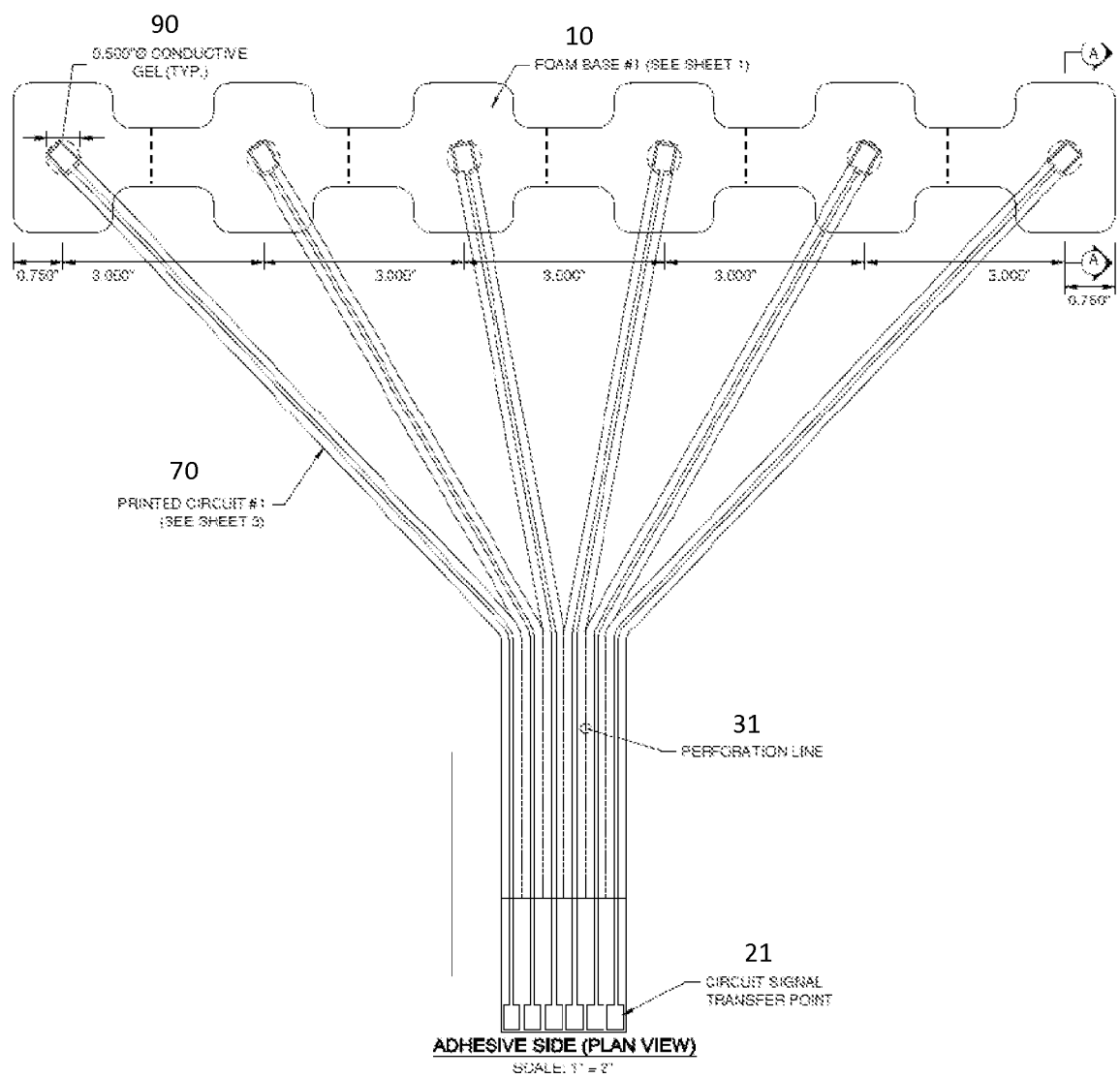
FIG. 50 depicts a bottom planar view of an embodiment of an expandable electrode pad of the present invention.
Figure 51:
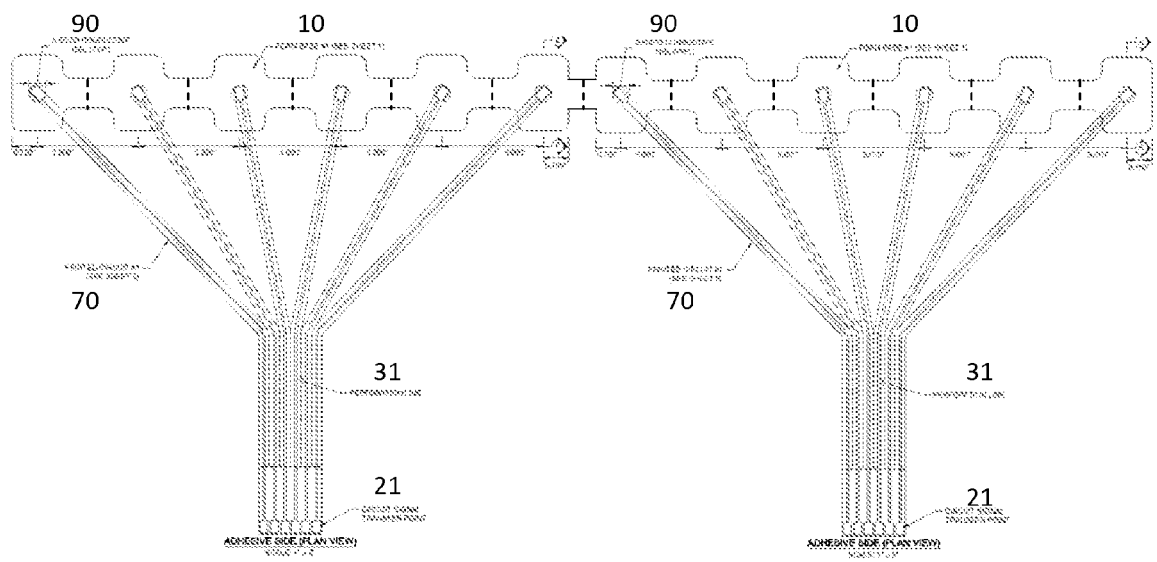
FIG. 51 depicts a bottom planar view of an embodiment of an expandable electrode pad of the present invention.
Figure 52:
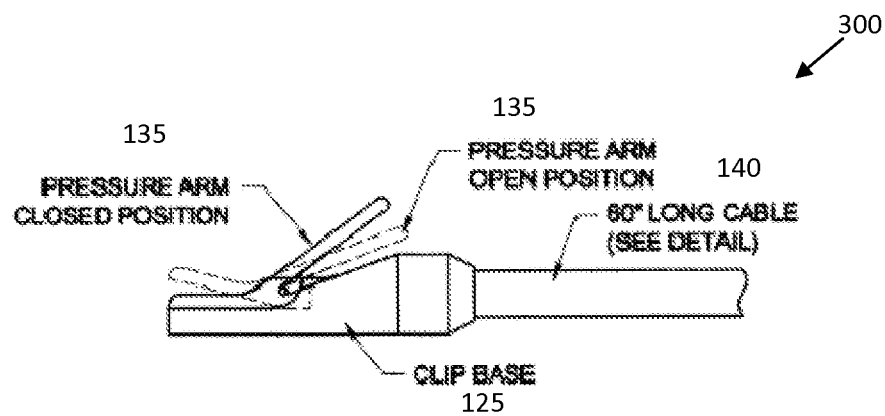
FIG. 52 depicts a side view of a cable connection assembly of the present invention.
Figure 53:
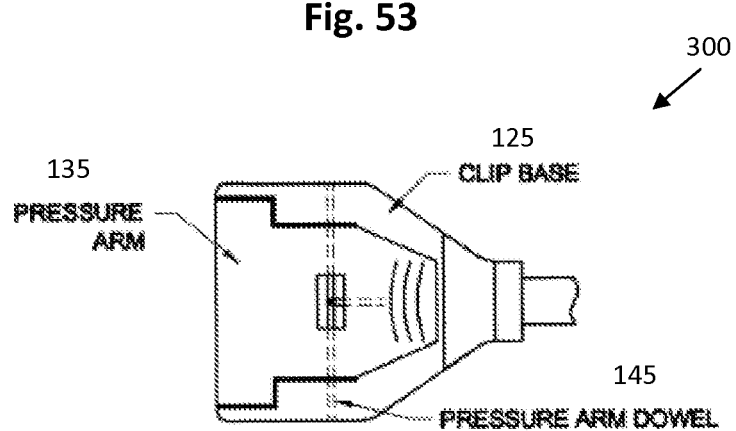
FIG. 53 depicts a top view of a cable connection assembly of the present invention.
Figure 54:
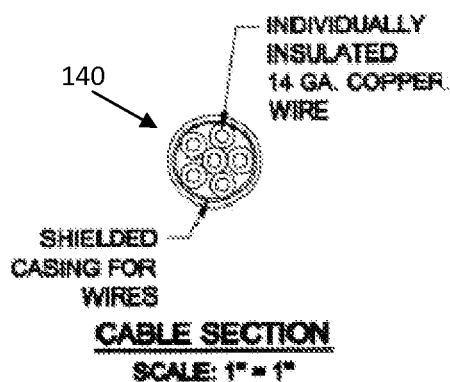
FIG. 54 depicts a cable cross sectional view of a cable connection assembly of the present invention.
Figure 55:
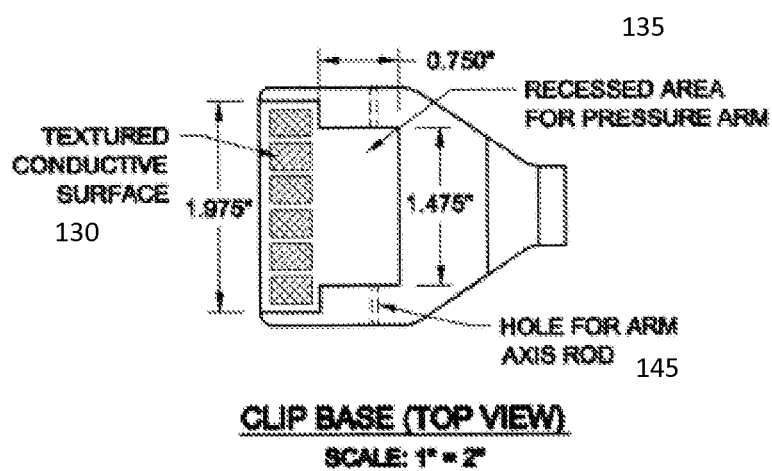
FIG. 55 depicts a clip base top view of a cable connection assembly of the present invention.
Figure 56:
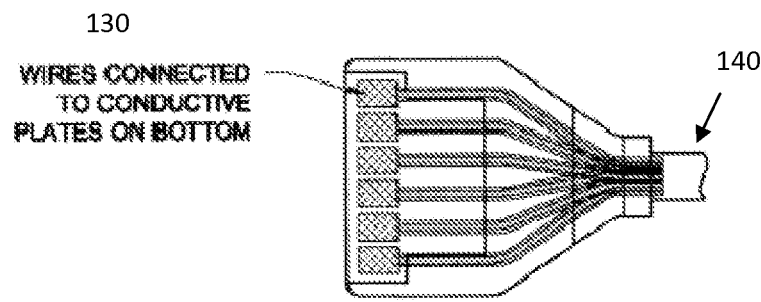
FIG. 56 depicts a top view of an embodiment of a wiring diagram of a cable connection assembly of the present invention.
Figure 57:
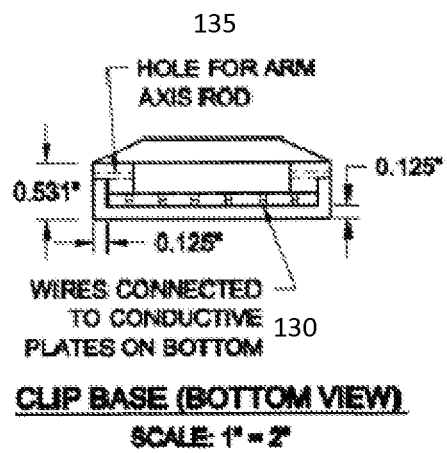
FIG. 57 depicts a clip base front view of a cable connection assembly of the present invention.
Figure 58:
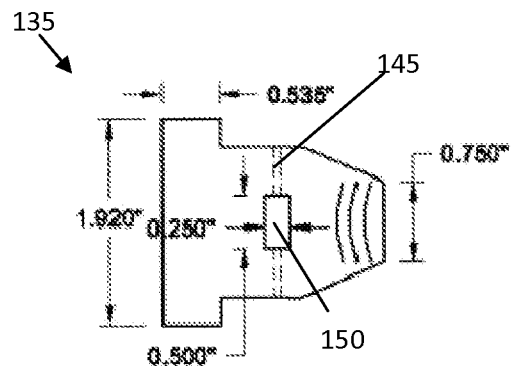
FIG. 58 depicts a pressure arm top view of a cable connection assembly of the present invention.
Figure 59:
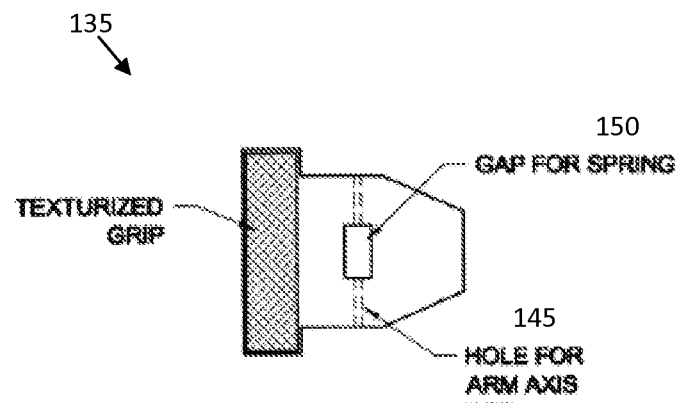
FIG. 59 depicts a pressure arm bottom view of a cable connection assembly of the present invention.
Figure 60:
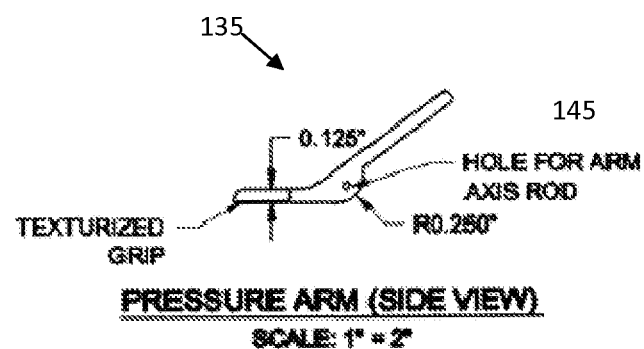
FIG. 60 depicts a pressure arm side view of a cable connection assembly of the present invention.

FIGS. 25-27 depict an office embodiment of a device of the present invention. The base member 10 of this exemplary embodiment is highly similar to that of the ambulance embodiment disclosed above, as seen from the six (6) electrode configuration within FIGS. 25-26. The distal contact 22 of each individual conductive circuit 70 may pass through the base material 10 or be attached to the bottom surface of the base material 10 (see FIG. 27). Each distal contact 22 may also be provided with a covering of conductive medium 90 to assist or enhance the electrical signal. The plurality of loose proximal contacts 21 may be attached to monitoring devices such as conventional doctor office 12-lead monitors (such as those using alligator-style clips), and the like. The base member 10 of the depicted embodiment may be stretched in any direction necessary so that each distal contact 22 may be properly positioned on patient anatomies of varying dimensions and sizes. Alternatively or additionally, perforations 31 may be disposed between two or more adjacent distal contacts 22, such as depicted in FIGS. 50-51, for allowing the individual electrodes or distal contacts 22 to be torn away from the primary base material 10 allowing for a greater reach distance when positioning the torn away base member 10 section and its associated distal contact 10.

Figure 28:
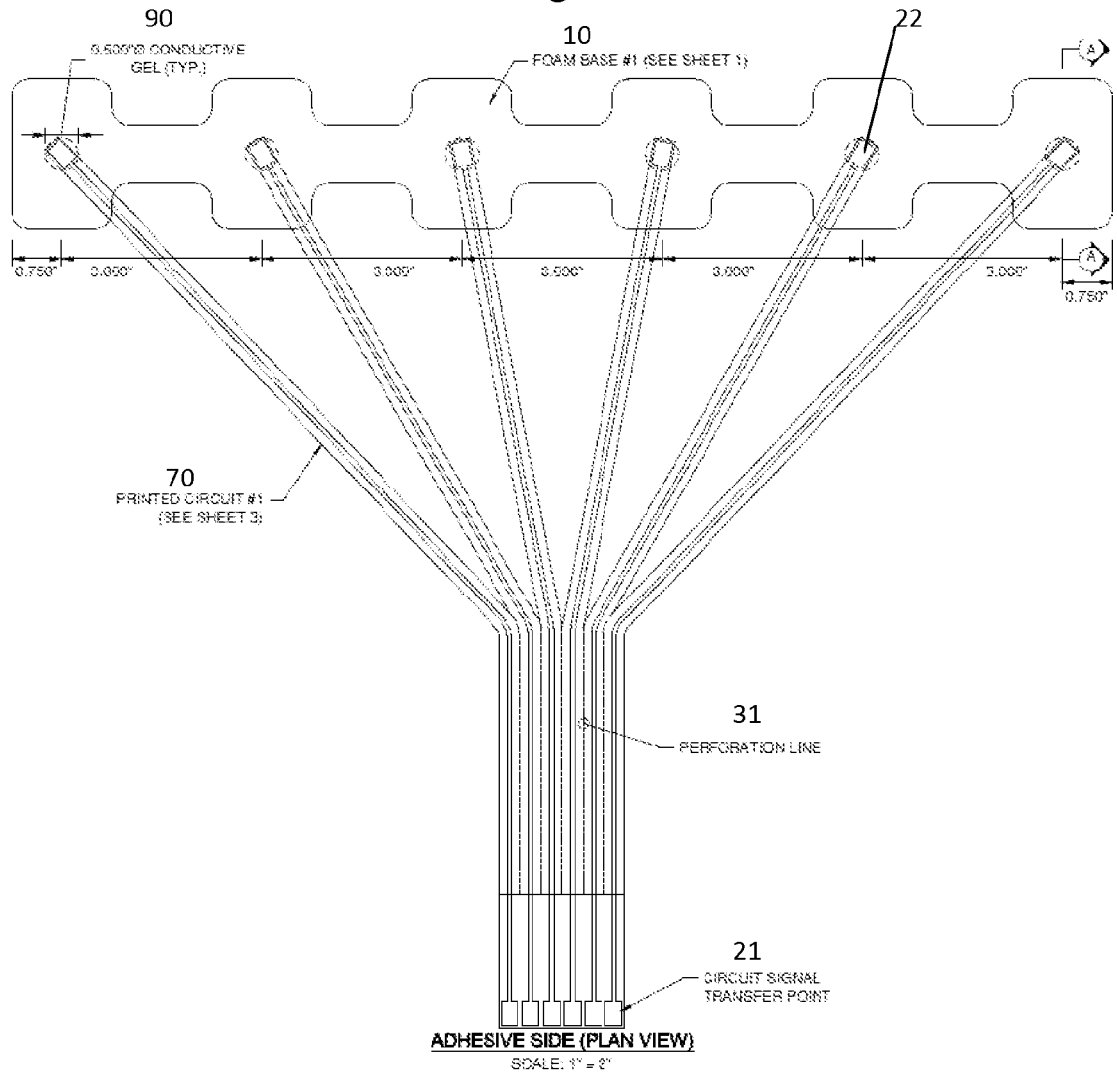
FIG. 28 depicts a bottom planar view of a "wireless" embodiment of the present invention.
Figure 29:
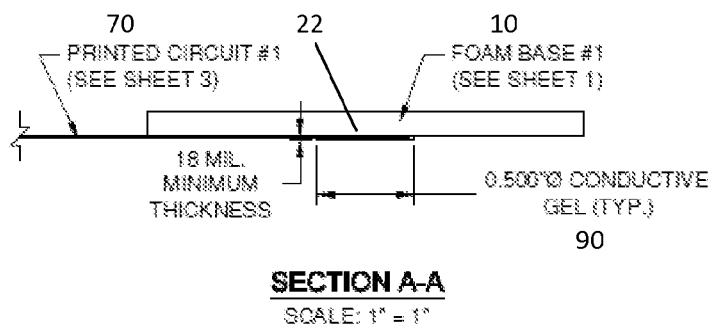
FIG. 29 depicts a side view of the "office" embodiment of the present invention.
Figure 30:
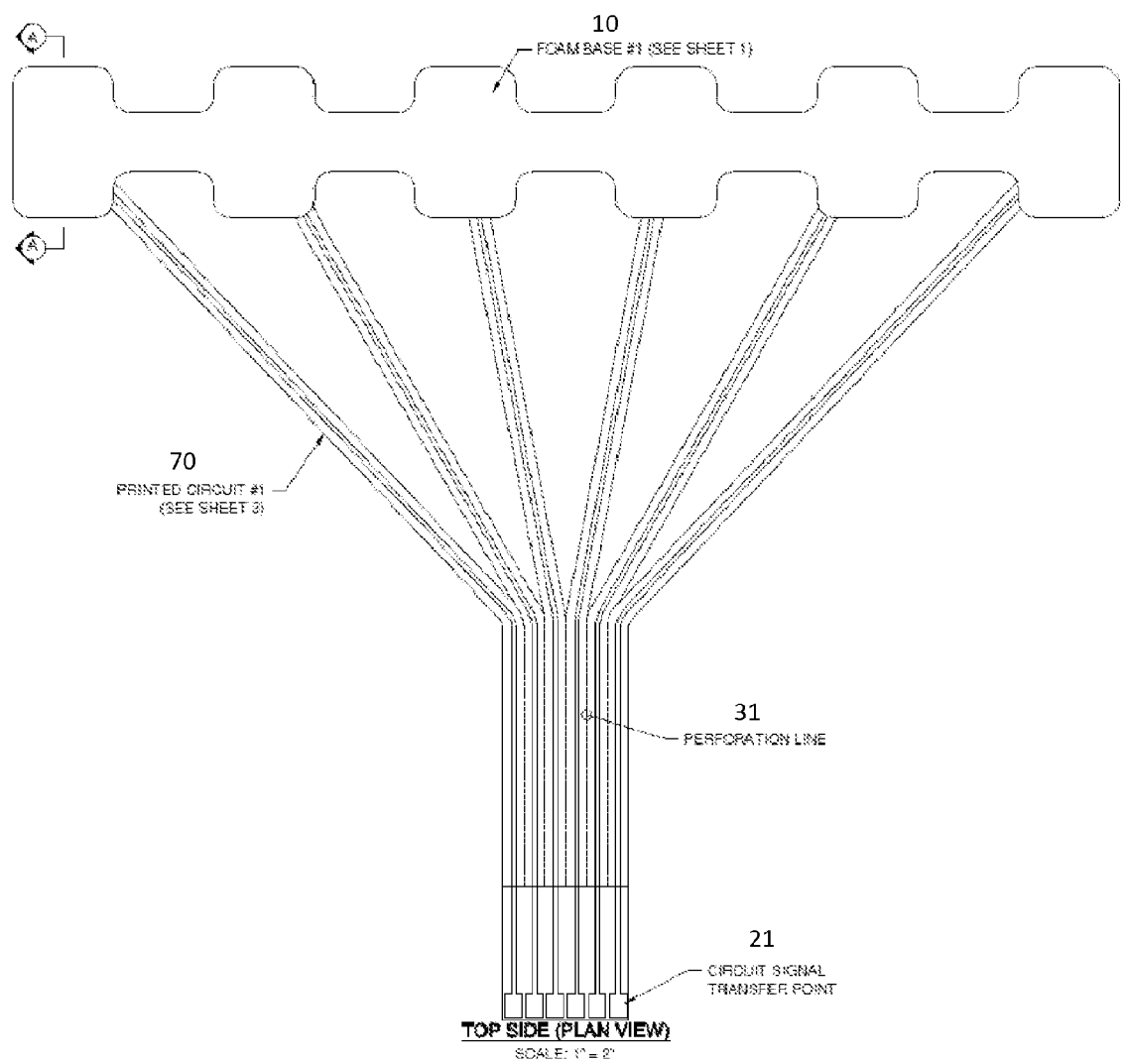
FIG. 30 depicts a top planar view of the "office" embodiment of the present invention.

FIGS. 28-30 depict a wireless embodiment of a device of the present invention. Such an embodiment shares common structures with the other disclosed embodiments and may further comprise a wireless unit (not shown) attached to the plurality of proximal contacts 21 for sending and/or receiving electrical signals. The base member 10 of this exemplary embodiment is highly similar to that of the ambulance and office embodiments disclosed above, as seen from the six (6) electrode configuration within FIGS. 28 and 30. The distal contact 22 of each individual conductive circuit 70 may pass through the base material 10 or be attached to the bottom surface of the base material 10 (see FIG. 29). Each distal contact 22 may also be provided with a covering of conductive medium 90 to assist or enhance the electrical signal. The plurality of proximal contacts 21 may attach to a wireless unit and thereby send and/or receive wireless transmissions to or from conventional monitoring devices and the like that are set up to receive and/or send wireless signals. The base member 10 of the depicted embodiment may be stretched in any direction necessary so that each distal contact 22 may be properly positioned on patient anatomies of varying dimensions and sizes. Alternatively or additionally, perforations 31 may be disposed between two or more adjacent distal contacts 22, such as depicted in FIGS. 50-51, for allowing the individual electrodes or distal contacts 22 to be torn away from the primary base material 10 allowing for a greater reach distance when positioning the torn away base member 10 section and its associated distal contact 10. Such wireless functionality may be incorporated onto every embodiment and device of the present invention.

Figure 31:
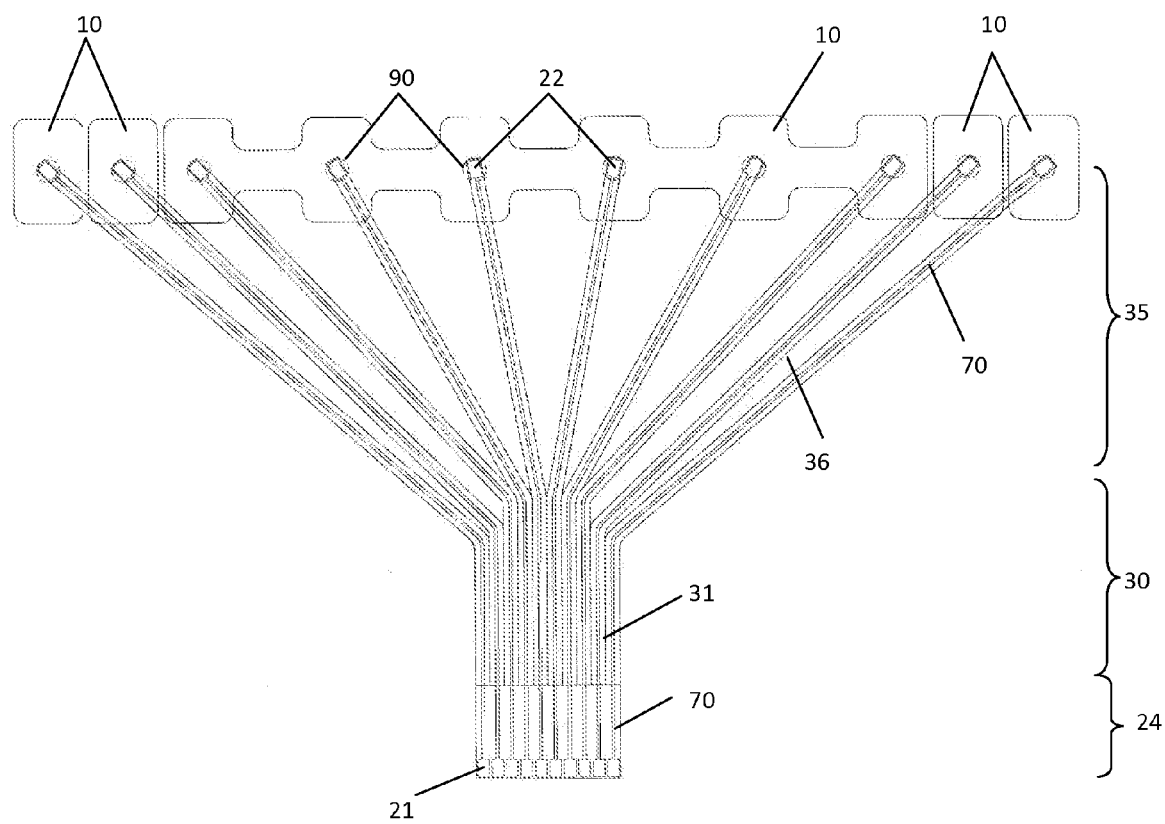
FIG. 31 depicts a bottom planar view of a "full" embodiment of the present invention.
Figure 32:
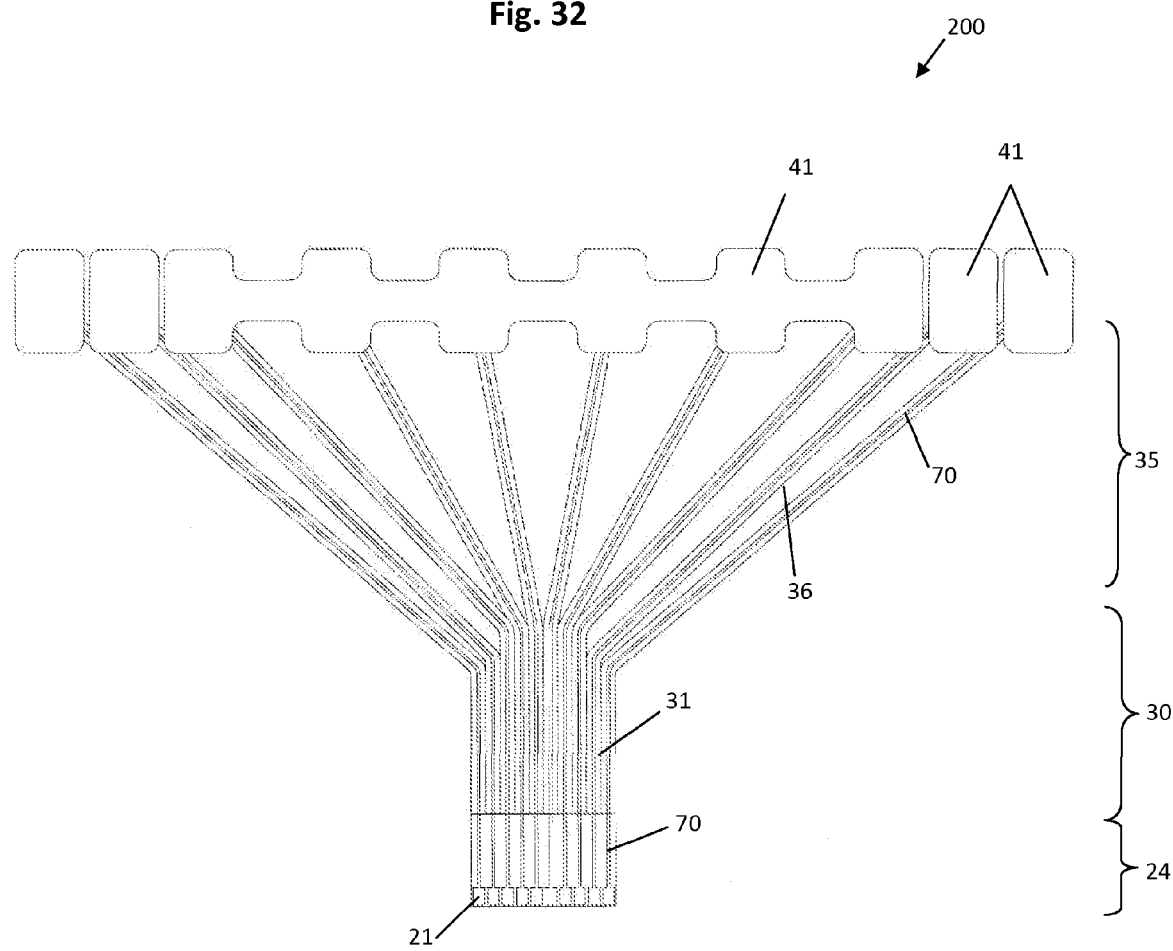
FIG. 32 depicts a top planar view of the "full" embodiment of the present invention.

FIGS. 31-35 depict a full embodiment of a device of the present invention. One exemplary embodiment of the full embodiment may comprise a 12-lead configuration requiring the placement of 10 electrodes on the patient's body. Four electrodes represent the patient's limbs and include the left arm electrode (LA), the right arm electrode (RA), the left leg electrode (LL), and the right leg electrode (RL). Six chest electrodes (V1-V6 leads) are placed on the patient's chest at various locations near the heart. Three additional references are constructed from measurements between the right arm and left arm (Lead I), the right arm and the left leg (Lead II) and the left arm to left leg (Lead III). The ten electrodes provide 12 measurement points consisting of I, II, III, AVR, AVL, AVF, and V1-V6 with the right leg electrode typically used as a ground. As shown in FIGS. 31-32, the RL, RA, LL, and LA electrodes and associated base member 10 portions may be separated from the primary base member 10 to allow for additional reaching distance for those leads in addition to the possibility of tearing perforations 31 within the perforated zone 30 to receive even more reaching distance if needed.

The base member 10 portions of this exemplary full embodiment are highly similar to those of the ambulance, office, and wireless embodiments disclosed above, as seen from the ten (6+4) electrode configuration within FIGS. 31-32. The distal contact 22 of each individual conductive circuit 70 may pass through the base material 10 or be attached to the bottom surface of the base material 10. Each distal contact 22 may also be provided with a covering of conductive medium 90 to assist or enhance the electrical signal. The plurality of proximal contacts 21 may attach to either a conventional monitoring device or a wireless unit and thereby send and/or receive wireless transmissions to or from conventional monitoring devices and the like that are set up to receive and/or send wireless signals. The base member 10 of the depicted embodiment may be stretched in any direction necessary so that each distal contact 22 may be properly positioned on patient anatomies of varying dimensions and sizes. Alternatively or additionally, perforations 31 may be disposed between two or more adjacent distal contacts 22, such as depicted in FIGS. 50-51, for allowing the individual electrodes or distal contacts 22 to be torn away from the primary base material 10 allowing for a greater reach distance when positioning the torn away base member 10 section and its associated distal contact 10.

Figure 33:
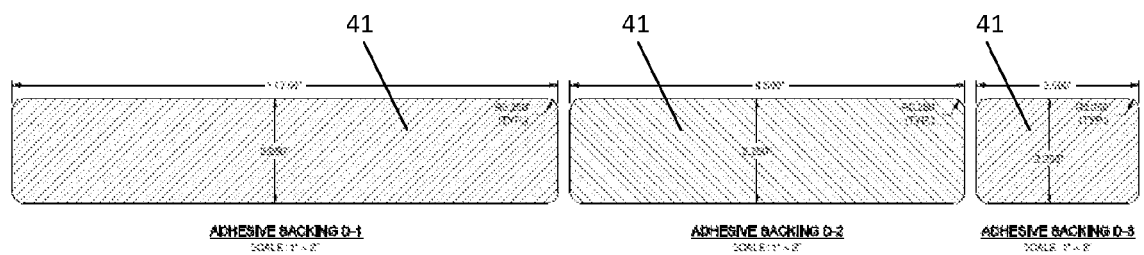
FIG. 33 depicts a planar view of an embodiment of releasable adhesive backing of the present invention.
Figure 34:
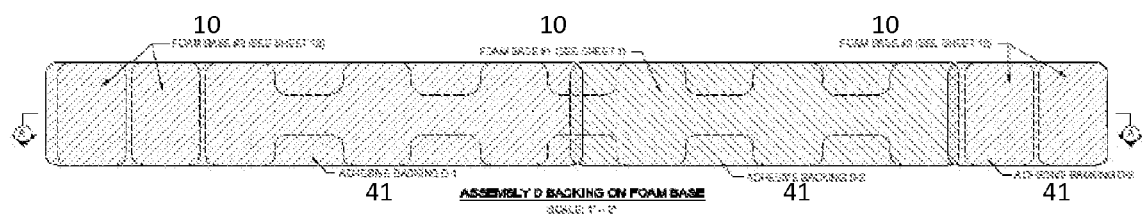
FIG. 34 depicts a bottom planar view of an embodiment of releasable adhesive backing of the present invention.
Figure 35:
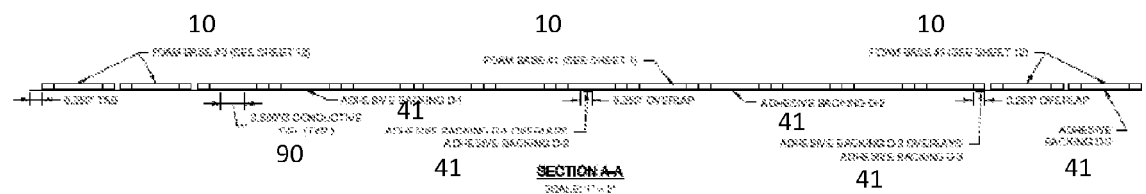
FIG. 35 depicts a side view of an embodiment of releasable adhesive backing of the present invention.
Figure 36:
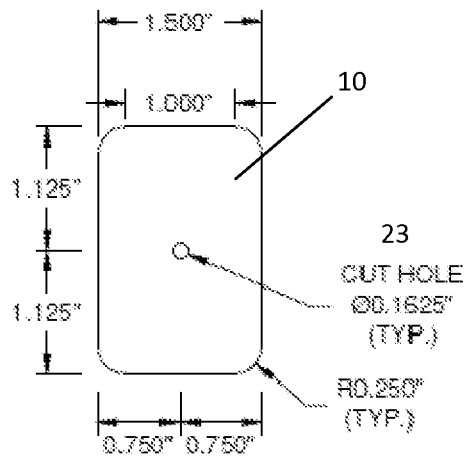
FIG. 36 depicts a planar view of an embodiment of a base member for use with one electrode of the present invention.
Figure 37:
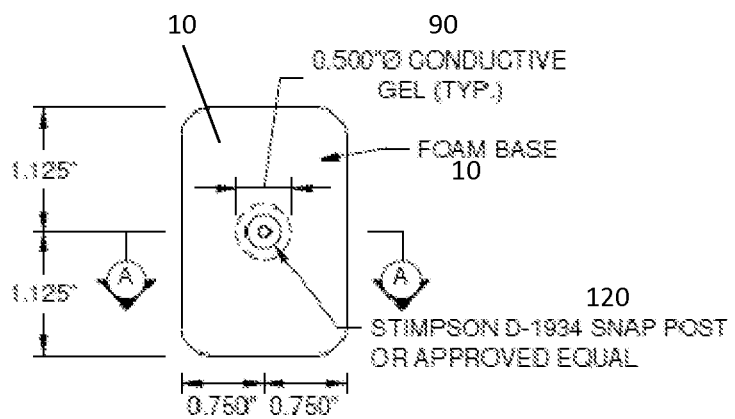
FIG. 37 depicts a bottom planar view of an embodiment of one electrode of the present invention.
Figure 38:
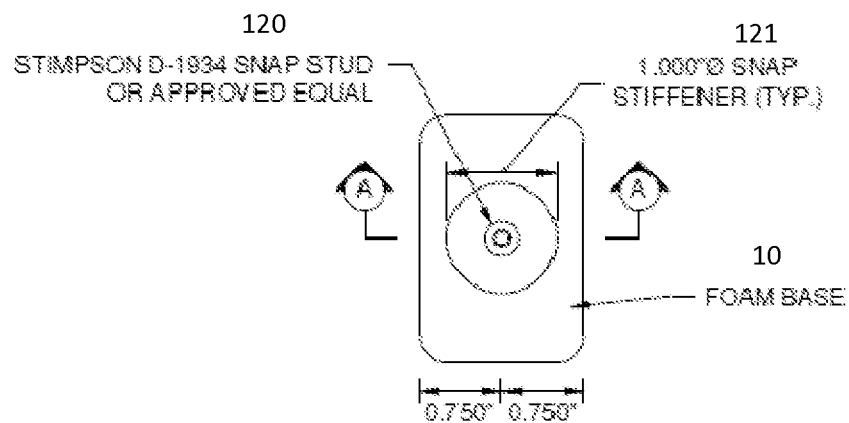
FIG. 38 depicts a top planar view of an embodiment of one electrode of the present invention.
Figure 39:
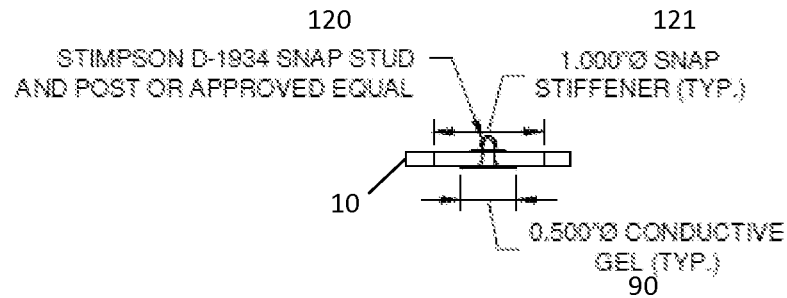
FIG. 39 depicts a side view of an embodiment of one electrode of the present invention.
Figure 40:
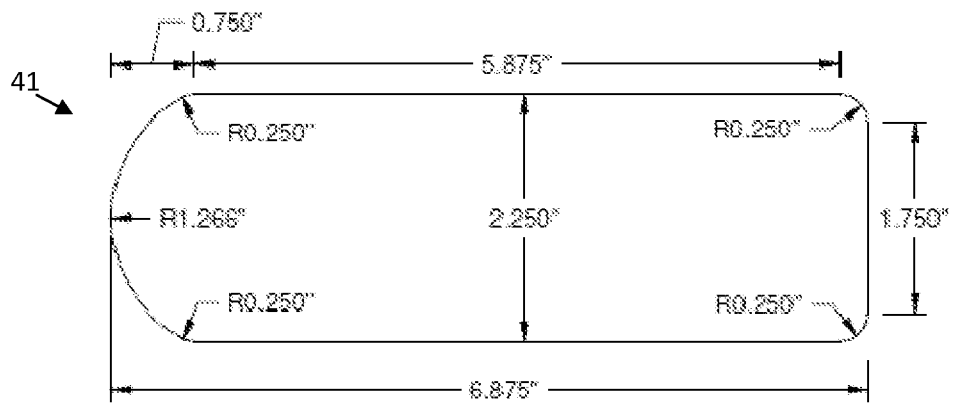
FIG. 40 depicts a planar view of an embodiment of releasable adhesive backing of the present invention.
Figure 41:
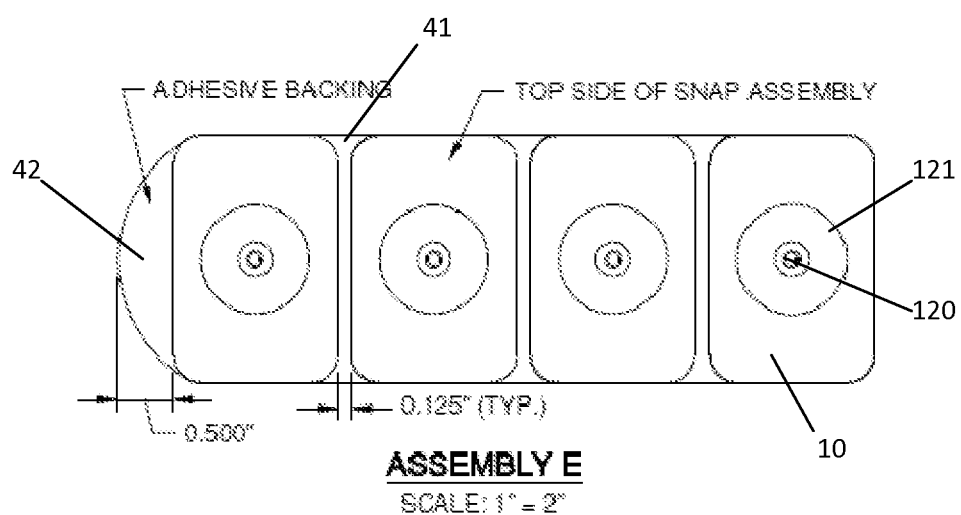
FIG. 41 depicts a top planar view of an embodiment of a "four electrode pad" embodiment of the present invention.
Figure 42:
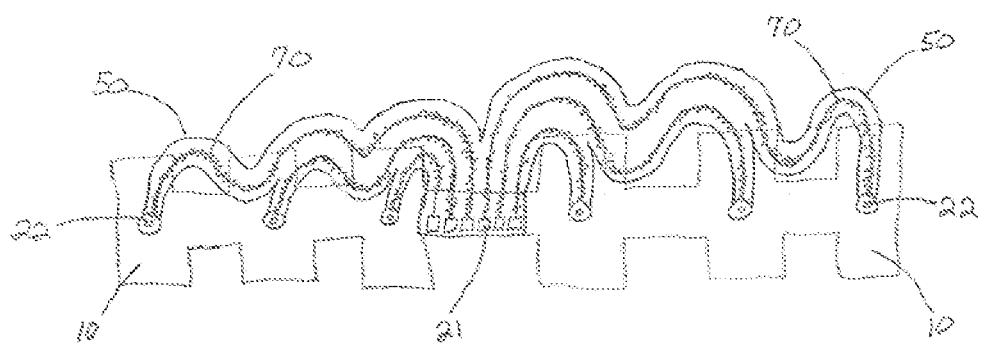
FIG. 42 depicts a top view of an embodiment of an expandable electrode pad of the present invention.
Figure 43:
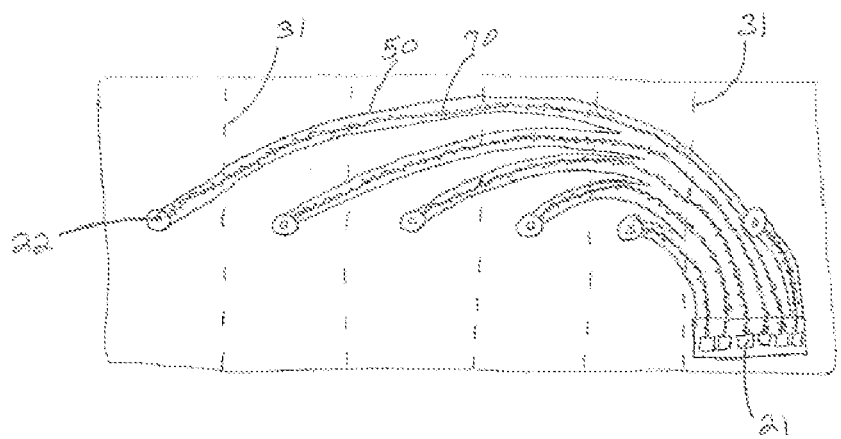
FIG. 43 depicts a top view of an embodiment of an expandable electrode pad of the present invention.
Figure 44:
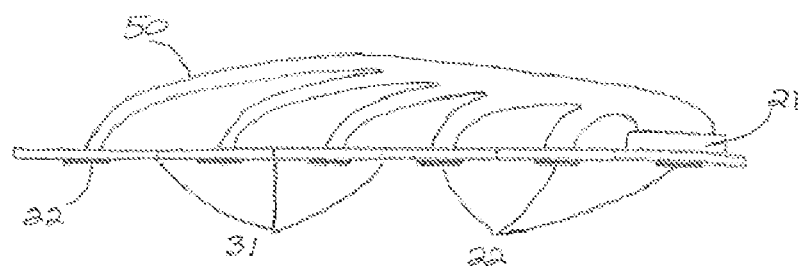
FIG. 44 depicts a top view of an embodiment of an expandable electrode pad of the present invention.
Figure 45:
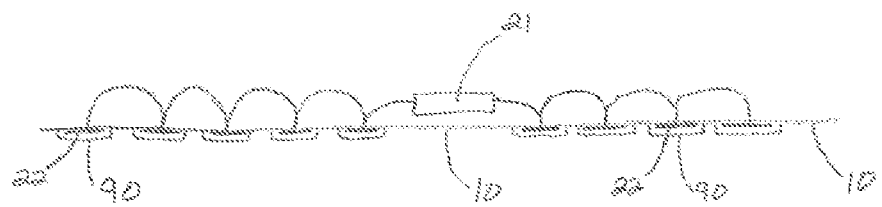
FIG. 45 depicts a top view of an embodiment of an expandable electrode pad of the present invention.

FIGS. 33-35 depict exemplary embodiments of releasable adhesive backings 41 configured to attach to the bottom surface of the base members 10 of the full embodiment depicted in FIGS. 31-32. Any number of adhesive backing 41 segments may be used, and FIGS. 33-35 depict the use of three portions of adhesive backing 41 being used to cover the various base member 10 portions and their and associated distal contacts 22. FIGS. 34-35 depict two overlap portions that assist a user in manipulating and grasping the overlapped portion thereby providing for rapid and efficient removal of the adhesive backing 41.

FIGS. 36-41 depict a four electrode embodiment of a device of the present invention. An embodiment of an individual base member and associated electrode or snap 120 is illustrated in FIGS. 36-39. The individual unit is identical to the ambulance embodiment disclosed above in FIGS. 14-18 and shares all of its structures with the exception being the exemplary shape of the base member 10 and each electrode unit starting without an attachment through the base member 10 to the other respective electrode units. A plurality of electrode units may be retained on one or more releasable adhesive backings 41 (see FIG. 41). This embodiment is not limited to the use of four electrode units and may comprise one or more individual electrode units disposed on one or more adhesive backings 41. The adhesive backing 41 may comprise any shape or configuration, wherein a preferred embodiment of an adhesive backing 41 follows the outer contour of the plurality of electrode units and may further provide a tab 42 to facilitate grasping of the adhesive backing 41 and removal of each electrode unit (see FIG. 40). Once the individual electrode units are positioned on the patient's body, conductive circuits 70 of the circuit body 20 may then attach to the snaps 120 or other electrode structure.

FIGS. 42-45 depict an alternate embodiments and configurations of a device of the present invention. Respective conductive circuits 70 connecting each distal contact 22 to a respective proximal contact 21 may comprise an extra length of material or "slack" thereby allowing the base member 10 to stretch without causing harm to the conductive circuit 70. As the base member 10 is stretched, the extra length of conductive circuit 70 (i.e. slack) is reduced accordingly. The plurality of proximal contacts 21 may provide a connecting structure to communicate with conventional monitoring devices or, alternatively, the plurality of proximal contacts 21 may connect to a wireless unit providing wireless communication to conventional monitoring devices set up to send and/or receive such wireless communications. The depicted embodiments within FIGS. 43 and 44 further include perforations 31 within the base member 10 between two or more adjacent distal contacts 22. The stretch characteristics and/or the ability for the base member 10 to tear away at the perforations 31 provide two methods alone or in combination that allow the plurality of distal contact 22 of the present inventive device to achieve additional reach distance thereby providing a one-size fits-all device for patients. As disclosed with previous embodiments, each of the plurality of distal contact 22 may also be provided with a covering of conductive medium 90 to assist or enhance the electrical signal.

Figure 46:
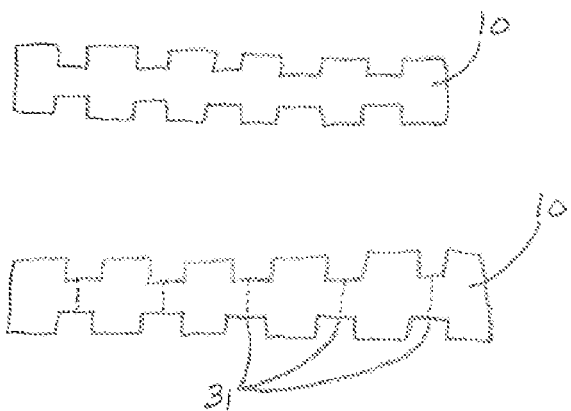
FIG. 46 depicts a top view of two embodiments of a base member of the present invention.
Figure 47:
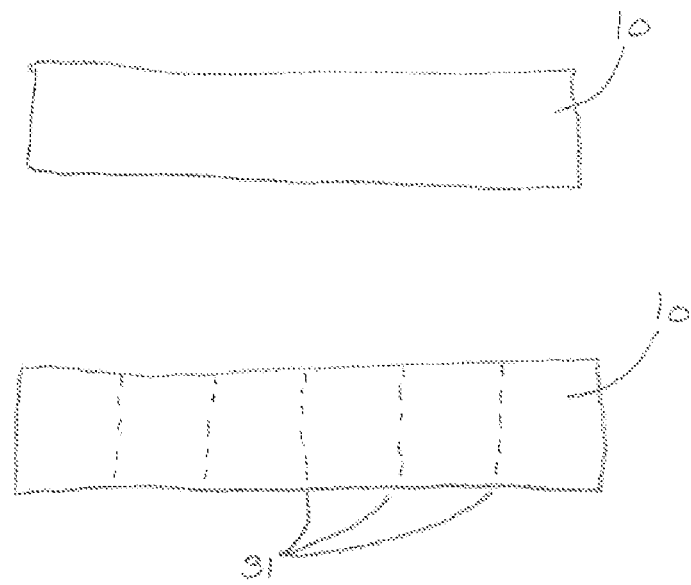
FIG. 47 depicts a top view of two embodiments of a base member of the present invention.
Figure 48:
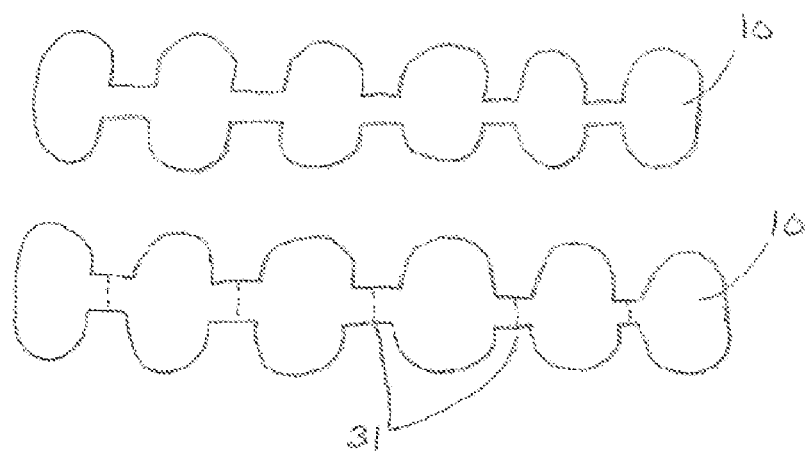
FIG. 48 depicts a top view of two embodiments of a base member of the present invention.
Figure 49:
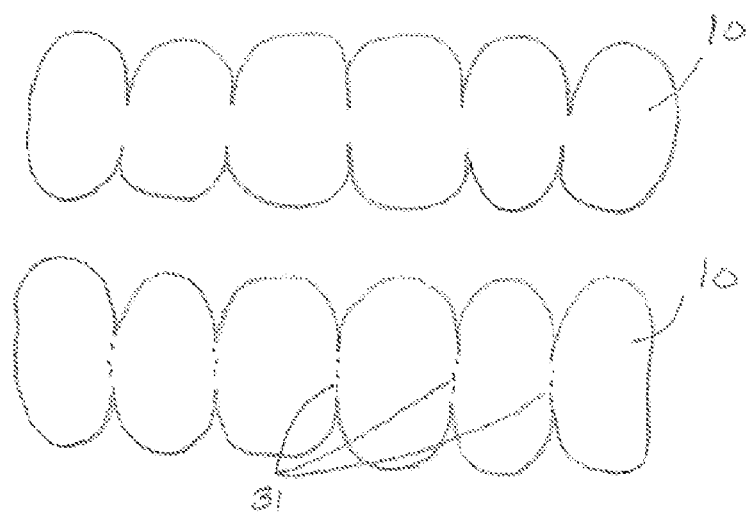
FIG. 49 depicts a top view of two embodiments of a base member of the present invention.

FIGS. 46-49 depict an exemplary assortment of base member 10 configurations. These embodiments are only shown as illustrative examples and base members 10 of the present invention may comprise any shape or configuration known within the art. FIG. 46 depicts generally rectangular base member 10 units connected by segments, wherein the connecting segments may or may not have perforations 31 therein. FIG. 47 depicts a generally rectangular base member 10, wherein the base member 10 may or may not have perforations 31 therein. FIG. 48 depicts generally oval base member 10 units connected by segments, wherein the connecting segments may or may not have perforations 31 therein. FIG. 49 depicts generally oval base member 10 units, wherein the oval base member 10 units may or may not have perforations 31 therebetween.

FIGS. 50-51 depict additional alternate embodiments of the present invention. FIG. 50 generally comprises a stretchable base member 10 having perforations 31 between each adjacent electrode unit and a circuit body 20 having a cut zone 35 located distal to a perforated zone 30. The perforations 31 within both the base member 10 and the perforation zone 30 of the circuit body 20 help reduce wire entanglement issues while providing a means to stretch and/or add reach length to each electrode unit as may be necessary for patients of all dimension and sizes. FIG. 51 depicts the use of multiple units of devices of the present invention to provide as many distal contacts 22 as are needed. All embodiments of the present invention may use any number of distal contacts 22 ranging from one to infinity. Additional distal contacts 22 may be provided as need for any current or future procedure by using multiple devices of the present invention as shown in FIG. 51, by constructing and providing devices of the present invention with the required number of distal contacts 22, by providing as many individual distal contacts 22 as are required (see FIGS. 36-41), and the like. Thus the present invention is freely expandable to new technologies that may require any number of additional leads and distal contacts 22.

FIGS. 52-60 depict an embodiment of a connector cable assembly 300 of the present invention. The connector cable assembly 300 may attach to the plurality of proximal contact 21 of the circuit body 20 of the present invention. The connector cable assembly 300 may comprise a clip base 125 having a plurality of conductive surfaces 130 for electrically communicating with said plurality of proximal contacts 21, a pressure arm 135 pivotable between and open and a closed configuration relative to the clip base 125, and a cable 140 extending from the clip base 125 proximally to an electrical monitoring device. The pressure arm 135 may be biased to the closed position for retaining the plurality of proximal contacts 21 therein. The bias of the pressure arm 135 may be provided by any method known within the art including but not limited to a spring 150 providing a the bias force by pivoting the pressure arm 135 about the axis of a dowel or rod 145 extending through the pressure arm 135 and into the clip base 125. While the connector cable assembly 300 depicted within FIGS. 52-60 is shown having a plurality of conductive surfaces 130 wherein six (6) conductive surfaces 130 are shown, the scope of the present invention includes any and all number of conductive surfaces 130 that may be incorporated into the connector cable assembly 300 of the present invention.

Generally speaking, and as shown in FIGS. 15, 23-24, 31, and 50, a snap 120 or a distal contact 22 of the circuit body 20 may pass through a contact aperture 23 within the base member 10 of the conductive circuit 70. As the base member 10 is stretched to fit larger people, the one or more conductive circuits 70 may separate (as needed) within the perforated zone 30 of the circuit body 20 via the perforations 31 disposed therein thereby allowing the base member 10 to stretch as needed without damaging the one or more individual conductive circuits 70. The base member may also, or alternatively, separate at perforations 31 disposed through the base member 10 material.

As the device is applied it is stretched to allow each contact 20 to be placed in the proper position on the patient's chest such that the conductive gel or other conductive medium 90 contacts the skin of the chest wall and receives or transmits electrical signals from or to the patient's body. Received electrical signals are transferred through the conductive medium 90 and then through the distal contact 22 and into the respective conductive circuits 70 that in turn transfer the signals to another device such that each signal is ultimately seen as a waveform. As the base member 10 is stretched to allow for the exact placement needed, the perforations 30 between the conductive circuits 70 within the perforated zone 30 separate allowing the base member 10 to move freely until attached to the chest wall with an adhesive that may be disposed on the bottom of the base member 10. If needed, the distal contacts 22 may be separated from the device and placed either as individual distal contacts 22 or as groups of distal contacts 22. For example, if a female wishes not to remove her bra or undergarments, the device can be separated and the V1 and V2 leads can be placed on the upper chest and the V3 through V6 leads can be placed on the lower chest area without removing the patient's bra or undergarments. In addition, if V4R is needed, the present inventive design allows for the V4 distal contact 22 to be separated and moved to the right chest area for evaluation of V4R.

In order to manufacture the device, the base member 10 can be stamped out and the distal contacts 22 poked or pushed through or adhered to the bottom of the base member 10. The conductive circuits 70 may be attached to their respective distal contact 20 with a wide variety of connection methods including but not limited to conductive gel, liquid paste, dry or powder conductive mediums 90 added to the bottom surface of each distal contact 20 to increase the electrical signal gathered, and the like. The conductive circuits 70 may be printed by any method of circuit printing known in the art.

The device 200 of the present invention may be configured to perform the majority of, if not all, cardiac monitoring. These additional duties and functions may be possible simply by changing the circuit connector at the plurality of proximal contacts 21, adding more contacts 20, and/or adding more perforations 31. The present inventive device 200 allows for placement of a distal contact 22 almost anywhere on a patient's body. This device 200 can be used for EEG (electroencephalogram) procedures, as addition to any other locations where an electrical impulse generated by the body would need to be gathered. The device 200 can be made one-size-fits-all, with a possible exception for infants and neonates.

The device 200 can be used by a person wishing to perform a 12-lead ECG on a patient having chest pains or for any other medically necessary reason. In use, the device 200 may be removed from its package and connected to the 12-lead monitor. The proper placements for the chest leads are then located. The V1 distal contact 22 is placed upon the skin directly over the fourth intercostal space just to the right side of the patient's sternum. The device 200 is then stretched, if necessary, and the V2 distal contact 22 is placed directly over the fourth intercostal space on the left side of the patient's sternum. The V4 distal contact 22 is then placed over the fifth intercostal space in the mid-clavicular area. The V3 distal contact 22 is then located between V2 and V4 forming a straight line. The V5 distal contact 22 is then placed halfway between V4 and the fifth intercostal space mid-auxiliary on the patient. The V6 distal contact 22 is then placed directly over the fifth intercostal space mid-auxiliary. The 12-lead machine may then be used to read the signal received from the placement of the device 200. Between every distal contact 22 placement occurring after the first distal contact 22 placement, the base member 10 of the device 200 may be stretched and/or the perforations 31 within the perforated zone 30 of the circuit body 20 may be torn to provide any further reach or positioning movement that is needed.

In alternative embodiments, the device 200 of the present invention can be used anywhere a disposable device is needed to gather electrical signals where the device 200 may accommodate various sizes and different shapes. As non-limiting examples, both a veterinarian and a brain surgeon may highly benefit from the use of a device 200 of the present invention. With increased insulation and/or greater electrode size, the present inventive device 200 may also have beneficial uses in electrical shock therapy. In non-medical uses, an electrician may use the instant device 200 to determine the exact location of an electrical short in circuits found in homes, cars, ships, and the like. Telephone companies and/or cable companies may also attach the present inventive device 200 to wires in order to read the electrical signals from the wires and thereby pinpoint signal leak locations.

Although a detailed description as provided in the attachments contains many specifics for the purposes of illustration, anyone of ordinary skill in the art will appreciate that many variations and alterations to the following details are within the scope of the invention. Accordingly, the following preferred embodiments of the invention are set forth without any loss of generality to, and without imposing limitations upon, the claimed invention. Thus the scope of the invention should be determined by the appended claims and their legal equivalents, and not by the examples given.

What is claimed is:

1. An expandable electrode pad comprising:
a base member having a top surface and a bottom surface, wherein said base member is composed of a stretchable material, wherein said base member comprises separate and distinct sections in the form of a plurality of base member units connected by connecting segments, wherein each base member unit has a first width, and each of said connecting segments has a second width; and
a plurality of distal contacts disposed along said bottom surface of said base member;
wherein said second width is less than said first width, and wherein each of said plurality of distal contacts is disposed in a base member unit, each base member unit having one distal contact disposed therein.

2. The expandable electrode pad of claim 1, wherein said base member further comprises a first plurality of perforations extending through said base member and disposed between at least two of said plurality of distal contacts.

3. The expandable electrode pad of claim 1, wherein said plurality of distal contacts comprises snaps disposed through said base member for communicating an electrical signal to or from a target surface adjacent said bottom surface of said base member.

4. The expandable electrode pad of claim 3, further comprising:
an adhesive disposed on said bottom surface of said base member; and
at least one releasable adhesive backing overlaying at least a portion of said adhesive.

5. The expandable electrode pad of claim 4, further comprising:
a plurality of conductive circuits, comprising:
a plurality of distal ends wherein each of said plurality of distal ends is electrically connected to one of said plurality of distal contacts; and
a plurality of proximal ends comprising a plurality of proximal contacts; and
circuit enclosure material surrounding each of said plurality of conductive circuits.

6. The expandable electrode pad of claim 5, further comprising:
a conductive medium covering each of said plurality of distal contacts for enhancing reception or transmission of an electrical signal.

7. The expandable electrode pad of claim 4, further comprising:
a plurality of conductive circuits, comprising:
a plurality of distal ends, wherein each of said plurality of distal ends comprises one of said plurality of distal contacts incorporated into one of said plurality of conductive circuits, respectively; and
a plurality of proximal ends comprising a plurality of proximal contacts; and
circuit enclosure material surrounding each of said plurality of conductive circuits.

8. The expandable electrode pad of claim 7, further comprising:
a conductive medium covering a lower surface of each of said snaps for enhancing reception or transmission of an electrical signal.

9. An expandable electrode pad comprising:
a base member having a top surface and a bottom surface, wherein said base member is composed of a stretchable material, wherein said base member comprises separate and distinct sections in the form of a plurality of base member units connected by connecting segments, wherein each base member unit has a first width, and each of said connecting segments has a second width said second width being less than said first width;
an adhesive disposed on said bottom surface of said base member;
at least one releasable adhesive backing overlaying at least a portion of said adhesive;
a plurality of conductive circuits, comprising:
a plurality of distal ends extending to said base member; and
a plurality of proximal ends comprising a plurality of proximal contacts; circuit enclosure material surrounding each of said plurality of conductive circuits; and
a plurality of snaps disposed through said base member wherein each of said snaps is capable of connecting to and electrically communicating with one of said plurality of distal ends of said plurality of conductive circuits, and wherein each snap of said plurality of snaps is disposed in a base member unit, each base member unit having one snap disposed therein.

10. The expandable electrode pad of claim 9, wherein said base member further comprises a first plurality of perforations extending through said base member and disposed between at least two of said plurality of distal ends of said plurality of conductive circuits.

11. The expandable electrode pad of claim 9, wherein said plurality of conductive circuits further comprises:
a perforated zone, wherein a second plurality of perforations extend through said circuit enclosure material in a linear arrangement between each adjacent conductive circuit of said plurality of conductive circuits wherein said second plurality of perforations are capable of being torn as needed to allow for extending the reach of each of said plurality of distal tips of said plurality of conductive circuits; and
a cut zone, wherein said cut zone is disposed distal to said perforated zone allowing freedom of movement between each of said plurality of distal ends of said plurality of conductive circuits.

12. The expandable electrode pad of claim 11, wherein said plurality of conductive circuits further comprises:
a fused zone disposed proximal to said perforated zone, wherein said circuit enclosure material maintains said plurality of conductive circuits in a parallel configuration at said plurality of proximal ends.

13. The expandable electrode pad of claim 12, further comprising:
a conductive medium covering a lower surface of each of said snaps for enhancing reception or transmission of an electrical signal.

14. The expandable electrode pad of claim 9, wherein each of said at least one releasable adhesive backings further comprises one or more tabs for facilitating removal of said at least one releasable adhesive backing.

15. The expandable electrode pad of claim 9, wherein adjacent said at least one releasable adhesive backings physically overlap allowing the overlapping portion to be easily grasped during removal.

16. The expandable electrode pad of claim 9, wherein said base member and said circuit enclosure material are both constructed from the same material.

17. The expandable electrode pad of claim 9, further comprising:
  a conductive medium covering each of said plurality of distal ends of said plurality of conductive circuits for enhancing reception or transmission of an electrical signal.

* * * * *